(12) United States Patent
Dudakov et al.

(10) Patent No.: US 9,119,824 B2
(45) Date of Patent: Sep. 1, 2015

(54) METHODS OF USE FOR IL-22 PROMOTING REJUVENATION OF THYMIC AND BONE MARROW FUNCTION

(75) Inventors: Jarrod Dudakov, New York, NY (US); Marcel van den Brink, New York, NY (US); Alan Hanash, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 275 days.

(21) Appl. No.: 13/474,319

(22) Filed: May 17, 2012

(65) Prior Publication Data
US 2014/0248235 A1 Sep. 4, 2014

Related U.S. Application Data

(60) Provisional application No. 61/487,517, filed on May 18, 2011.

(51) Int. Cl.
*A61K 38/20* (2006.01)
*C07K 14/54* (2006.01)
(52) U.S. Cl.
CPC .................................. *A61K 38/20* (2013.01)
(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | 435/6.11 |
| 4,683,202 A | 7/1987 | Mullis | 435/91.2 |
| 4,965,188 A | 10/1990 | Mullis et al. | 435/6.12 |
| 7,226,591 B2 | 6/2007 | Gurney et al. | 424/130.1 |
| 2002/0193305 A1* | 12/2002 | Ruben et al. | 514/12 |
| 2003/0100076 A1 | 5/2003 | Gurney et al. | 435/69.52 |
| 2011/0052554 A1 | 3/2011 | Zakrzewski et al. | 424/93.71 |

OTHER PUBLICATIONS

Weiss et al. Cloning of murine IL-22 receptor alpha 2 and comparison with its human counterpart. Genes and Immunity vol. 5, 330-336 (2004).*
Sano et al. Stat3 in Thymic Epithelial Cells Is Essential for Postnatal Maintenance of Thymic Architecture and Thymocyte Survival. Immunity, vol. 15, 261-273 (Aug. 2001).*
Xie et al. Interleukin (IL)-22, a Novel Human Cytokine That Signals through the Interferon Receptor-related Proteins CRF2-4 and IL-22R. The Journal of Biological Chemistry vol. 275/40:31335-31339 (2000).*
Aujla and Kolls, "IL-22: A Critical Mediator in Mucosal Host Defense." *J Mol Med (Berl)*, 87(5):451-454 (2009).
Awasthi, et al., "Cutting Edge: IL-23 Receptor Gfp Reporter Mice Reveal Distinct Populations of IL-17-Producing Cells." *J Immunol*, 182(10):5904-5908 (2009).
Boniface, et al., "IL-22 Inhibits Epidermal Differentiation and Induces Proinflammatory Gene Expression and Migration of Human Keratinocytes." *J Immunol*, 174(6):3695-3702 (2005).
Cella, et al., "A Human Natural Killer Cell Subset Provides an Innate Source of IL-22 for Mucosal Immunity." *Nature*, 457(7230):722-725 (2009).
Cella, et al., "Expansion of Human NK-22 Cells with IL-7, IL-2, and IL-1beta Reveals Intrinsic Functional Plasticity." *Proc Natl Acad Sci U S A*, 107(24):10961-10966 (2010).
Gray, et al., "Developmental Kinetics, Turnover, and Stimulatory Capacity of Thymic Epithelial Cells." *Blood*, 108(12):3777-3785 (2006).
Gray, et al., "Unbiased Analysis, Enrichment and Purification of Thymic Stromal Cells." *J Immunol Methods*, 329(1-2):56-66 (2008).
Guo and Topham, "Interleukin-22 (IL-22) Production by Pulmonary Natural Killer Cells and the Potential Role of IL-22 During Primary Influenza Virus Infection." *J Virol*, 84(15):7750-7759 (2010).
Heng, et al., "Getting Back at Nature: Understanding Thymic Development and Overcoming Its Atrophy." *Curr Opin Pharmacol*, 10(4):425-433 (2010).
Hollander, et al., "Emerging Strategies to Boost Thymic Function." *Curr Opin Pharmacol*, 10(4):443-453 (2010).
Hughes, et al., "Interleukin-1beta Selectively Expands and Sustains Interleukin-22+ Immature Human Natural Killer Cells in Secondary Lymphoid Tissue." *Immunity*, 32(6):803-814 (2010).
Kim, et al., "Ox40 Ligand and CD30 Ligand Are Expressed on Adult but Not Neonatal CD4+CD3− Inducer Cells: Evidence That IL-7 Signals Regulate CD30 Ligand but Not Ox40 Ligand Expression." *J Immunol*, 174(11):6686-6691 (2005).
Liang, et al., "Interleukin (IL)-22 and IL-17 Are Coexpressed by Th17 Cells and Cooperatively Enhance Expression of Antimicrobial Peptides." *J Exp Med*, 203(10):2271-2279 (2006).
Mak, et al., "Knockout Mice: A Paradigm Shift in Modern Immunology." *Nat Rev Immunol*, 1(1):11-19 (2001).
Manley, "Thymus Organogenesis and Molecular Mechanisms of Thymic Epithelial Cell Differentiation." *Semin Immunol*, 12(5):421-428 (2000).
Manley and Condie, "Transcriptional Regulation of Thymus Organogenesis and Thymic Epithelial Cell Differentiation." *Prog Mol Biol Transl Sci*, 92:103-120 (2010).

(Continued)

*Primary Examiner* — Elizabeth C Kemmerer
*Assistant Examiner* — Regina M Deberry
(74) *Attorney, Agent, or Firm* — Heslin Rothenberg Farley & Mesiti P.C.

(57) ABSTRACT

The present invention provides methods and compositions for the use of IL-22 to promote thymic growth following thymic insult. In particularly preferred embodiments, the present invention provides methods of using therapeutic IL-22 compositions for treating patients with thymic atrophy and alterations in bone marrow derived white blood cells, including cancer patients undergoing chemotherapy, patients exposed to radiation (i.e. cancer therapy, nuclear disaster, terrorist attack, etc.), patients with HIV infections/AIDS, patients with organ transplantation, aging patients, and the like. In a further embodiment, therapeutic IL-22 compositions are contemplated as a prophylactic to boost immune response when additional T-cell function is needed, i.e. to boost immune response during vaccination.

10 Claims, 24 Drawing Sheets

(56) References Cited

OTHER PUBLICATIONS

Figure 1:
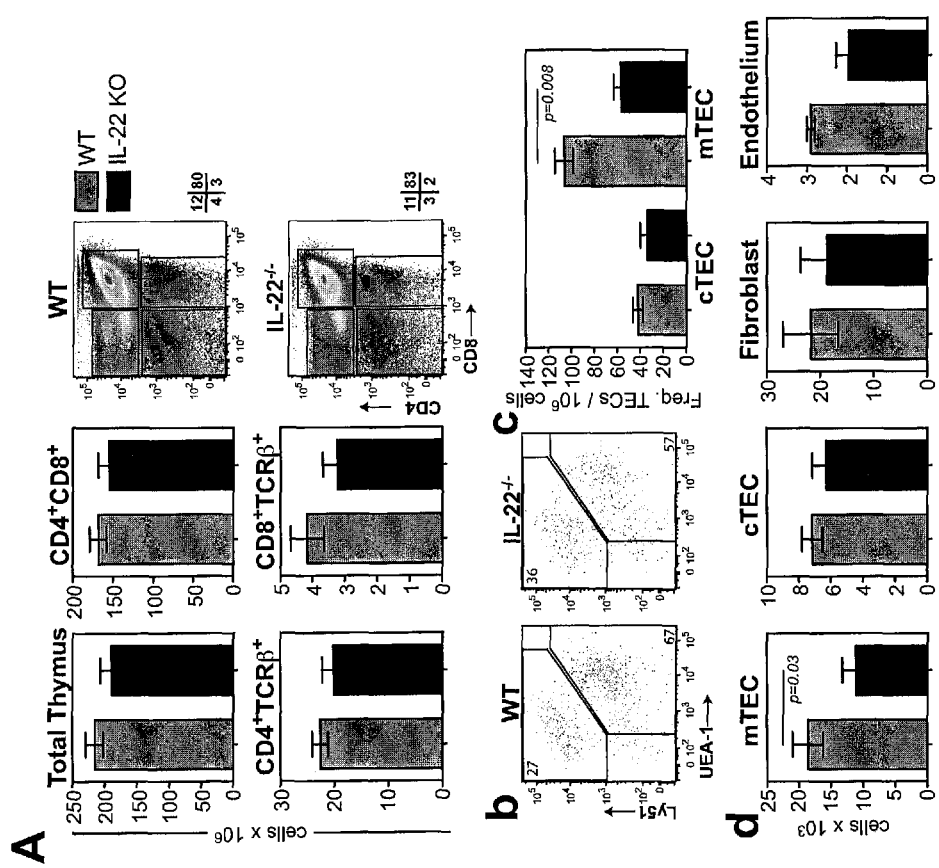

Maury, et al., "Prolonged Immune Deficiency Following Allogeneic Stem Cell Transplantation: Risk Factors and Complications in Adult Patients." *Br J Haematol*, 115(3):630-641 (2001).

Petrie and Zuniga-Pflucker, "Zoned Out: Functional Mapping of Stromal Signaling Microenvironments in the Thymus." *Annu Rev Immunol*, 25:649-679 (2007).

Pickert, et al., "STAT3 Links IL-22 Signaling in Intestinal Epithelial Cells to Mucosal Wound Healing." *J Exp Med*, 206(7):1465-1472 (2009).

Purton, et al., "Expression of the Glucocorticoid Receptor from the 1a Promoter Correlates with T Lymphocyte Sensitivity to Glucocorticoid-Induced Cell Death." *J Immunol*, 173(6):3816-3824 (2004).

Rossi, et al., "Rank Signals from CD4(+)3(−) Inducer Cells Regulate Development of Aire-Expressing Epithelial Cells in the Thymic Medulla." *J Exp Med*, 204(6):1267-1272 (2007).

Sawa, et al., "Lineage Relationship Analysis of RORgammat+ Innate Lymphoid Cells." *Science*, 330(6004):665-669 (2010).

Sawa, et al., "RORgamma(t)+ Innate Lymphoid Cells Regulate Intestinal Homeostasis by Integrating Negative Signals from the Symbiotic Microbiota." *Nat Immunol*, 12(4):320-326 (2011).

Siddiqui, et al., "E-Cadherin Marks a Subset of Inflammatory Dendritic Cells That Promote T Cell-Mediated Colitis." *Immunity*, 32(4):557-567 (2010).

Small, et al., "Comparison of Immune Reconstitution after Unrelated and Related T-Cell-Depleted Bone Marrow Transplantation: Effect of Patient Age and Donor Leukocyte Infusions." *Blood*, 93(2):467-480 (1999).

Sonnenberg, et al., "Border Patrol: Regulation of Immunity, Inflammation and Tissue Homeostasis at Barrier Surfaces by IL-22." *Nat Immunol*, 12(5):383-390 (2011).

Spits and Di Santo, "The Expanding Family of Innate Lymphoid Cells: Regulators and Effectors of Immunity and Tissue Remodeling." *Nat Immunol*, 12(1):21-27 (2011).

Storek, et al., "T Cell Reconstitution after Bone Marrow Transplantation into Adult Patients Does Not Resemble T Cell Development in Early Life." *Bone Marrow Transplant*, 16(3):413-425 (1995).

Storek, et al., "Infectious Morbidity in Long-Term Survivors of Allogeneic Marrow Transplantation Is Associated with Low CD4 T Cell Counts." *Am J Hematol*, 54(2):131-138 (1997).

Storek, et al., "Immunity of Patients Surviving 20 to 30 Years after Allogeneic or Syngeneic Bone Marrow Transplantation." *Blood*, 98(13):3505-3512 (2001).

Sun, et al., "Requirement for RORgamma in Thymocyte Survival and Lymphoid Organ Development." *Science*, 288(5475):2369-2373 (2000).

Tachiiri, et al., "Genomic Structure and Inducible Expression of the IL-22 Receptor Alpha Chain in Mice." *Genes Immun*, 4(2):153-159 (2003).

Takatori, et al., "Lymphoid Tissue Inducer-Like Cells Are an Innate Source of IL-17 and IL-22." *J Exp Med*, 206(1):35-41 (2009).

van den Brink, et al., "Strategies to Enhance T-Cell Reconstitution in Immunocompromised Patients." *Nat Rev Immunol*, 4(11):856-867 (2004).

Wolk, et al., "Cutting Edge: Immune Cells as Sources and Targets of the IL-10 Family Members?" *J Immunol*, 168(11):5397-5402 (2002).

Wolk, et al., "IL-22 Increases the Innate Immunity of Tissues." *Immunity*, 21(2):241-254 (2004).

Wolk, et al., "IL-22 Regulates the Expression of Genes Responsible for Antimicrobial Defense, Cellular Differentiation, and Mobility in Keratinocytes: A Potential Role in Psoriasis." *Eur J Immunol*, 36(5):1309-1323 (2006).

Wolk, et al., "Maturing Dendritic Cells Are an Important Source of IL-29 and IL-20 That May Cooperatively Increase the Innate Immunity of Keratinocytes." *J Leukoc Biol*, 83(5):1181-1193 (2008).

Wolk, et al., "Biology of Interleukin-22." *Semin Immunopathol*, 32(1):17-31 (2010).

Zakrzewski, et al., "Adoptive Transfer of T-Cell Precursors Enhances T-Cell Reconstitution after Allogeneic Hematopoietic Stem Cell Transplantation." *Nat Med*, 12(9):1039-1047 (2006).

Zakrzewski, et al., "Enhancing T Cell Reconstitution after Hematopoietic Stem Cell Transplantation: A Brief Update of the Latest Trends." *Blood Cells Mol Dis*, 40(1):44-47 (2008).

Zenewicz, et al., "Innate and Adaptive Interleukin-22 Protects Mice from Inflammatory Bowel Disease." *Immunity*, 29(6):947-957 (2008).

Zheng, et al., "Interleukin-22, a T(H)17 Cytokine, Mediates IL-23-Induced Dermal Inflammation and Acanthosis." *Nature*, 445(7128):648-651 (2007).

Zheng, et al., "Interleukin-22 Mediates Early Host Defense against Attaching and Effacing Bacterial Pathogens." *Nat Med*, 14(3):282-289 (2008).

Dudakov, et al., "Interleukin-22 Drives Endogenous Thymic Regeneration in Mice." Science, 336(6077):91-5. Epub Mar. 1, 2012.

\* cited by examiner

Table 1: IL-22 administration enhances thymic regeneration after irradiation

| | TBI Alone | | | | Ly5.1 → B6 | | | |
|---|---|---|---|---|---|---|---|---|
| | Day 7 | | Day 28 | | Day 7 | | Day 28 | |
| | PBS | IL-22 | PBS | IL-22 | PBS | IL-22 | PBS | IL-22 |
| ETP[a] | 0.4 ± 0.07 | 0.8 ± 0.01* | 5.7 ± 1.1 | 19.1 ± 2.1** | 1.29 ± 0.5 | 2.7 ± 0.9 | 49.5 ± 13.5 | 53.3 ± 0.8 |
| DN1[b] | 0.5 ± 0.04 | 0.8 ± 0.1* | 2.3 ± 0.3 | 6.6 ± 0.8** | 3.2 ± 0.8 | 8.7 ± 1.6** | 9.8 ± 2.3 | 12.4 ± 1.5 |
| DN2[b] | 0.03 ± 0.002 | 0.05 ± 0.005 | 0.9 ± 0.2 | 3.1 ± 0.8* | 1.6 ± 0.5 | 4.0 ± 1.1* | 5.3 ± 1.5 | 5.4 ± 0.7 |
| DN3[b] | 7.7 ± 0.5 | 11.5 ± 0.7 | 13.6 ± 2.9 | 38.1 ± 8.4** | 23.2 ± 5.6 | 62.1 ± 12* | 29.9 ± 6.1 | 41.7 ± 5.7 |
| DN4[b] | 10.3 ± 1.5 | 50.7 ± 24 | 24.6 ± 4.2 | 68.2 ± 7.8** | 8.9 ± 2.7 | 27.7 ± 2.3** | 45.3 ± 5.8 | 78.5 ± 6.6** |
| DP[c] | 38.6 ± 4.5 | 47.4 ± 4.9 | 30.8 ± 4.7 | 134 ± 24.3** | 0.15 ± 0.02 | 0.25 ± 0.02** | 185 ± 29.2 | 207 ± 16.9 |
| CD4+ SP[c] | 0.14 ± 0.01 | 0.19 ± 0.02 | 1.3 ± 0.3 | 5.1 ± 1.5* | 0.3 ± 0.09 | 0.7 ± 0.02 | 107 ± 11 | 149 ± 12** |
| CD8+ SP[c] | 0.51 ± 0.04 | 0.09 ± 0.02* | 3.2 ± 0.7 | 9.5 ± 1.6** | 0.4 ± 0.09 | 0.6 ± 0.07 | 40.2 ± 3.8 | 47.1 ± 4.8 |
| mTEC[d] | 1.1 ± 0.1 | 2.5 ± 0.5* | 10.8 ± 4.1 | 31.8 ± 5.4* | 1.8 ± 0.7 | 5.3 ± 0.4** | 33.8 ± 6.7 | 61.0 ± 7.9** |
| cTEC[d] | 0.9 ± 0.2 | 2.0 ± 0.3* | 14.1 ± 5.7 | 51.0 ± 0.9* | 2.4 ± 0.7 | 3.8 ± 0.5 | 27.8 ± 3.6 | 48.8 ± 6.2* |
| Endothelium[d] | 0.3 ± 0.1 | 1.3 ± 0.5* | 1.5 ± 0.5 | 6.9 ± 1.6** | 8.6 ± 2.7 | 32.5 ± 7.9* | 4.1 ± 1.0 | 7.3 ± 0.6* |
| Fibroblast[d] | 0.4 ± 0.2 | 0.2 ± 0.05 | 1.6 ± 0.5 | 3.9 ± 1.5 | 35.6 ± 12.7 | 116 ± 17.6** | 4.67 ± 0.7 | 8.1 ± 1.0 | a, × 10³;
b, × 10⁵;
c, × 10⁶;
d, × 10⁴.

Figure 2-2

METHODS OF USE FOR IL-22 PROMOTING REJUVENATION OF THYMIC AND BONE MARROW FUNCTION

CROSS REFERENCE TO RELATED APPLICATIONS

This application claims priority to U.S. Provisional Application No. 61/487,517, filed on May 18, 2011.

This invention was made with government support from the National Institutes of Health; grant numbers R01HL69929, CA107096, AI080455 and HL095075 in addition to the United States Department of Defense USAMRAA Award W81XWH-09-1-0294 and the Radiation Effects Research Foundation (RERF-NIAID). The United States Government has certain rights in the invention.

FIELD OF THE INVENTION

The present invention provides methods and compositions for the use of IL-22 to promote thymic growth following thymic insult. In particularly preferred embodiments, the present invention provides methods of using therapeutic IL-22 compositions for treating patients with thymic atrophy and alterations in bone marrow derived white blood cells, including cancer patients undergoing chemotherapy, patients exposed to radiation (i.e. cancer therapy, nuclear disaster, terrorist attack, etc.), patients with HIV infections/AIDS, patients with organ transplantation, aging patients, and the like. In a further embodiment, therapeutic IL-22 compositions are contemplated as a prophylactic to boost immune response when additional T-cell function is needed, i.e. to boost immune response during vaccination.

BACKGROUND OF THE INVENTION

Thymopoiesis is a highly complex process involving crosstalk interactions between developing thymocytes and their supporting stromal microenvironment. The stromal environment contains a system for 'training' T lineage progenitor T cells as developing thymocytes for proper binding of a T cell receptor recognizing 'self' in the context of a peptide. Progenitor T cells pass through three main developmental stages starting as 'double-negative' and progressing to mature functional T cells as they pass through the thymic cortex, cortico-medullary junction and medulla. Mature functional T cells are necessary for disease and cancer prevention in addition to maintaining the immunological health of an individual.

The main stromal compartments responsible for guiding developing thymocytes are lined with thymic epithelial cells (TEC). These cells are damaged by radiation exposure, chemotherapy, viral infections, certain immunosuppressant compounds in addition to age-induced atrophy. Damage to the thymic stromal cells increases the rate of atrophy that in turn reduces the functional capability of the thymus to properly train and generate T cells.

Thus, there remains a need for compositions and methods for restoring the capability of the thymus to support thymopoiesis after damage of the thymic epithelial cells (TECs).

SUMMARY OF THE INVENTION

In one embodiment, the present invention provides methods and compositions for the use of IL-22 to promote thymic growth following thymic insult. In particularly preferred embodiments, the present invention provides methods of using therapeutic IL-22 compositions for treating patients with thymic atrophy and alterations in bone marrow derived white blood cells, including cancer patients undergoing chemotherapy, patients exposed to radiation (i.e. cancer therapy, nuclear disaster, terrorist attack, etc.), patients with HIV infections/AIDS, patients with organ transplantation, aging patients, and the like. In a further embodiment, therapeutic IL-22 compositions are contemplated as a prophylactic to boost immune response when additional T-cell function is needed, i.e. to boost immune response during vaccination.

In one embodiment, the invention relates to method of treatments for increasing thymic epithelial cell (TEC) function. Thus in some embodiments, the invention provides a method of treatment for increasing thymic epithelial cell (TEC) function comprising: a) providing: i) a composition comprising an IL-22 protein, and ii) a population of thymic epithelial cells, wherein at least a portion of said cells have reduced function (e.g. as measured by an in vitro assay); and b) contacting said thymic epithelial cells (e.g. the entire population containing the portion with reduced function or just the portion having reduced function) with said IL-22 protein composition such that at least a portion of said thymic epithelial cells having reduced function display increased function. In some embodiments, said IL-22 protein is human IL-22. In some embodiments, said reduced function is thymic epithelial cells having a lowered capability to produce mature thymocytes. In some embodiments, an in vitro assay shows reduced T cell production. In some embodiments, said reduced function is thymic epithelial cells producing a lower number of mature functional thymocytes. In some embodiments, said increased function is thymic epithelial cells having an increase in capability to produce mature thymocytes.

In some embodiments, said increased function is thymic epithelial cells producing an increased number of mature functional thymocytes.

In some embodiments, the invention provides a method of treatment, comprising, a) providing: i) a therapeutic IL-22 composition comprising an IL-22 protein, and ii) a subject having a population of thymic epithelial cells wherein at least a portion of said cells have reduced function; and b) administering said therapeutic IL-22 composition to said subject under conditions for increasing thymic epithelial cell function. In some embodiments, said subject is an immunocompromised patient. It is not meant to limit the type of patient. Indeed, in some embodiments, said subject has a condition selected from the group consisting of, but not limited to, thymic atrophy, alterations in bone marrow derived white blood cells, chemotherapy treatment, exposure to radiation (i.e. cancer therapy, nuclear disaster, terrorist attack, etc.), human immunodeficiency virus infections, acquired immunodeficiency syndrome (AIDS), organ transplantation and aging related loss of thymus cell function, prophylactically to boost immune response when additional T-cell function is needed, i.e. to boost immune response during vaccination, and the like. In some embodiments, said subject has cancer. In some embodiments, said reduced function is thymic epithelial cells producing a lower number of mature functional thymocytes. In some embodiments, said increased function is thymic epithelial cells producing an increased number of mature functional thymocytes.

In some embodiments, the invention provides a method of treatment for enhancing production of bone marrow derived lymphoid cells, comprising, a) providing: i) a therapeutic IL-22 composition comprising an IL-22 protein, and ii) a subject having a condition of altered bone marrow immune cell generation, such that bone marrow derived stem cells have decreased lymphoid cells; and b) administering said therapeutic IL-22 composition to said subject under conditions for enhancing production of bone marrow derived lymphoid cells. In some embodiments, said subject is an immunocompromised patient. It is not meant to limit the type of patient. Indeed, in some embodiments, said subject has a condition selected from the group consisting of, but not limited to, alterations in bone marrow derived white blood cells, chemotherapy treatment, exposure to radiation (i.e. cancer therapy, nuclear disaster, terrorist attack, etc.), human immunodeficiency virus infections, acquired immunodeficiency syndrome (AIDS), organ transplantation and aging related loss of bone marrow cell function. In some embodiments, said subject is an irradiated subject. In some embodiments, said subject has cancer. In some embodiments, said IL-22 is human IL-22. In some embodiments, said IL-22 composition is administered as a cell transplant wherein said cell is an IL-22 secreting cell. In some embodiments, said IL-22 secreting cell is a LTi cell. In some embodiments, said IL-22 secreting cell is a cell transformed with a Lentivirus construct for expressing IL-22. In some embodiments, said IL-22 secreting cell is a preT (precursor T) cell transformed with a Lentivirus construct for expressing IL-22. In some embodiments, said decreased lymphoid cells is bone marrow cells producing a reduced number of mature functional lymphoid cells. In some embodiments, said enhancing production of bone marrow derived lymphoid cells results in an increased number of mature functional lymphoid cells. In some embodiments, said method further comprises administering a composition comprising IL-23. In some embodiments, said method further comprises administering IL-23.

In some embodiments, the invention provides a method of treatment, comprising, a) providing: i) a therapeutic IL-22 composition comprising an IL-22 protein, and ii) a subject having a condition of altered bone marrow cells, such that bone marrow derived white blood cells have increased myeloid cells and decreased lymphoid cells; and b) administering said therapeutic IL-22 composition to said subject under conditions for decreasing production of bone marrow derived myeloid cells and increasing production of bone marrow derived lymphoid cells.

DEFINITIONS

To facilitate an understanding of the present invention, a number of terms and phrases are defined below:

As used herein, "thymic epithelial cells" or "TECs" refers to an epithelial cell located in the thymus, including cortical thymic epithelial cells (cTECs) and medullary TECs (mTECs).

As used herein, "bone marrow cells" or "bone marrow" refers to a cell found in the bone marrow, i.e. a bone marrow derived stem cell, such as a lymphoid cell (bone marrow derived lymphoid cell), in particular, cells ranging in differentiation stages from stem cells to mature cells, including lymphoid and myeloid cells, stromal cells, etc. Examples of bone marrow stem cells include hematopoietic stem cells and mesenchymal stem cells. Examples of bone marrow cells include, white blood cells (leukocytes), red blood cells (erythrocytes), platelets (thrombocytes), osteoblasts, chondrocytes, and myocytes.

The term "IL-22 polypeptide" or "IL-22" or "IL22" or "IL-22 protein" as used herein refers to a biologically active polypeptide capable of producing the thymic and bone marrow derived lymphocytes described herein. Exemplary specific polypeptide sequences are described in U.S. Patent Appln. No. US2003/0100076 and U.S. Pat. No. 7,226,591, herein incorporated by reference in their entirety. The IL-22 polypeptides used herein may be isolated from a variety of sources, such as from human tissue types or from another source, or prepared by recombinant or synthetic methods. For example, descriptions of the preparation of, purification of, derivation of, formation of antibodies to or against, administration of, compositions containing, treatment of a disease with, etc., pertain to each polypeptide of the invention individually. Additionally, the IL-22 for use in the present inventions may be a product of a recombinant method wherein the IL-22 encoding DNA is administered to a subject, for example, such as cell therapy or viral therapy. The term "IL-22 polypeptide" also includes variants of the IL-22 polypeptides. The IL-22 of the present invention may also be modified in a way to form a chimeric molecule comprising IL-22 fused to another, heterologous polypeptide or amino acid sequence.

As used herein, the term "altered function" refers to a change in function, either increasing a function or decreasing a function, for example, a change in cell numbers, such as total thymocytes, a change in cell type, such as a change in the number of pre B cells, a change in the number of CD8+ cells, a change in function, such as epithelial cells capable of secreting a specific cytokine or inducing survival or maturation of a specific cell type, and the like.

For the purposes of the present invention, "increasing" or "increased" or "upregulated" or "enhanced" or "display increased function" or "increased function" or "enhancing" in relation to function, refers to a higher level of an action or a cell type, such as an increased number of a specific cell type, i.e. mature functional thymocytes or bone marrow lymphoid cells, or an amount of a compound compared to a control or wild-type, such as increased production of a cytokine, a molecule activation, such as TECs with increased function have increased levels of STAT1, STAT3 and STAT-5, see, for example, FIG. 5B) increased function may increase a cell type, such as when "myeloid cell production is increased" or when "lymphoid cell production is increased", etc., for example, treating TECs with IL-22 as described herein increased production of single positive CD4+ T cells, and the like, and when treating bone marrow cells, in vivo, increased cell function of bone marrow cells increased lymphoid cells, for example, increased immature B cells, a pre-B cell, etc., a myeloid cell type, such as granulocytes, macrophages, etc., or increasing cytokine production, such as IL-22 production, etc.

Thus, examples of increased mature functional lymphoid cells from bone marrow are increased (enhanced) numbers of at least one lymphoid cell type, such as immature B cells, a pre-B cell, etc. Further, examples of contemplated enhanced or enhancing function may also refer to enhancing immocompetence, such as methods wherein immunocompromised patients having reduced immune function, such as reduced T-cell antigen receptor repertoires, reduced cytokine secretion, reduced proliferative responses to antigen, and the like, are treated with compositions comprising IL-22 resulting in increased immune function. Increased immune function may be measured as an increase in any one of T-cell antigen receptor repertoires, cytokine secretion, proliferative responses to antigen, ability to respond to infections, and the like.

For the purposes of the present invention, "decreasing" or "decreased" or "reduced" or "reduced function" or "downregulated" or "having reduced function" refers to a lower level of production compared to a control or wild-type, such that "cells have reduced function" such as a reduced cell type, reduced lymphoid cells, such as reduced cell numbers, etc. In general, thymic epithelial cells with reduced function, such as caused by total body radiation, have reduced numbers of cells, etc. As another example, a reduced function may be a lowered production of a cytokine, i.e. IL-22 in knock-out (KO) mice compared to IL-22+/+ or wild-type mice and mice with IL-22 "knocked out" as described herein having decreased production of thymic single positive cells. As other examples, a reduced function is thymic epithelial cells producing a lower number of mature functional thymocytes, a decreased function is bone marrow cells producing a reduced number of mature functional lymphoid cells, bone marrow derived stem cells have decreased numbers of lymphoid cells. In other words, a reduced function may also be an altered function, for one example, altered bone marrow immune cell generation may show that bone marrow derived stem cells have (or produce) decreased lymphoid cells. Having a reduced function is not meant to be a static result. In some embodiments, contacting or administering an IL-22 composition of the present inventions may alter a function, such as when IL-22 induces cells having reduced function to display increased function, see Examples.

As used herein, an in vitro assay refers to any in vitro assay used to measure the increase or decrease of function or number of cells or cell subtypes. Readouts for in vitro assays could include for examples, flow cytometry measurements of thymocytes and T cell subtypes, granulocytes, stromal cells, proliferation, apoptosis, etc., see assays used in the Examples.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein, particularly in reference to a "human subject." For the purposes of the present inventions, a subject may be immunocompromised, i.e. not able to fight off infections or control abnormal cell growth. Examples of immunocompromised subjects include subjects that have any of the following conditions, thymic atrophy, alterations in bone marrow derived white blood cells, chemotherapy, exposure to radiation, deliberate irradiation, human immunodeficiency virus infections, organ transplantation and aging related loss of thymus function, etc.

The terms "treatment", "treating" and the like are used herein to generally mean obtaining a desired pharmacological and/or physiological effect. In relation to a therapeutic treatment of subject the effect may be prophylactic in terms of completely or partially preventing a disease or symptom thereof and/or may be therapeutic in terms of partially or completely curing a disease and/or adverse effect attributed to the disease. Thus "treatment" refers to both therapeutic treatment and prophylactic or preventative measures, wherein the object is to prevent or slow down (lessen) the targeted pathologic condition or disorder. Subjects in need of treatment include those already with the disorder as well as those prone to have the disorder or those in whom the disorder is to be prevented.

As used herein, when referring to a method of the present invention the term "treatment" covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease. The present invention is directed towards treating patients with medical conditions relating to a loss of immunocompetence, e.g. thymic atrophy, from a treatment related to a disease such as irradiation, chemotherapy, immunosuppression, etc. Accordingly, a treatment of the invention would involve preventing, inhibiting or relieving any medical condition where a desired level of immunocompetence would be achieved by the use of an IL-22 composition of the present inventions. In certain embodiments, treatment refers to exposing a subject to a therapy directed towards treating a disease, such as irradiation, chemotherapy, and the like.

As used herein, the term "administering" or "administration" refers to the act of giving a drug, prodrug, pharmaceutical composition, or other agent, or therapeutic treatment (e.g., a composition of the present invention) to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), mucosal (e.g., oral mucosa or buccal), rectal, ear, by injection (e.g., intravenously, subcutaneously, intratumorally, intraperitoneally, etc.) and the like. Administration "in combination with" one or more further therapeutic agents includes simultaneous (concurrent) and consecutive administration in any order.

As used herein, the term "pharmaceutical" or "therapeutic" in reference to a composition refers to the combination of an active agent (for example, in an effective amount) (e.g., such as an IL-22 protein or IL-22 DNA)) with a carrier, inert or active, making the composition especially suitable for diagnostic or therapeutic use in vitro, in vivo or ex vivo (in vitro).

An "effective amount" of a polypeptide disclosed herein or an agonist or antagonist thereof is an amount sufficient to carry out a specifically stated purpose. An "effective amount" may be determined empirically and in a routine manner, in relation to the stated purpose.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also may include stabilizers and preservatives. Examples of carriers, stabilizers, and adjuvants are described in the art (See e.g., Martin, Remington's Pharmaceutical Sciences, 15th Ed., Mack Publ. Co., Easton, Pa. (1975), incorporated herein by reference).

The terms "pharmaceutically acceptable" or "pharmacologically acceptable," as used herein, refer to compositions that do not substantially produce adverse reactions (e.g., toxic, allergic, or immunological reactions) when administered to a subject.

As used herein, "cytokine" refers to a protein or glycoprotein that is used in an organism as signaling compounds. It is intended to include homologues and synthetic versions. Examples include IL-22, the IL-10 family, IL-7, the interferon (IFN) family, CC chemokines, CXC chemokines, and the like.

As used herein the term "biologically active polypeptide" refers to any polypeptide which maintains a desired biological activity, for example, activities as described herein, such as increasing mature B cells, increasing thymic cell function, and the like.

Where "amino acid sequence" is recited herein to refer to an amino acid sequence of a naturally occurring protein molecule, "amino acid sequence" and like tetrns, such as "polypeptide" and "protein" are not meant to limit the amino acid sequence to the complete, native amino acid sequence associated with the recited protein molecule.

The term "recombinant protein" or "recombinant polypeptide" as used herein refers to a protein molecule that is expressed from a recombinant DNA molecule (e.g. human IL-22 expressed by cells containing a plasmid or virus with the human IL-22 gene).

As used herein, the term "portion" when used in reference to a protein (as in "a portion of a given protein") refers to fragments of that protein. The fragments may range in size from four amino acid residues to the entire amino sequence minus one amino acid.

The term "recombinant DNA molecule" as used herein refers to a DNA molecule that is comprised of segments of DNA joined together by means of molecular biological techniques (e.g. a human IL-22 gene ligated into a plasmid DNA sequence or viral sequence).

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "gene" refers to a nucleic acid (e.g., DNA) sequence that comprises coding sequences necessary for the production of a polypeptide or precursor. It is intended that the term encompass polypeptides encoded by a full length coding sequence, as well as any portion of the coding sequence, so long as the desired activity and/or functional properties (e.g., enzymatic activity, ligand binding, etc.) of the full-length or fragmented polypeptide are retained. The term also encompasses the coding region of a structural gene and the sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as "5' untranslated sequences." The sequences that are located 3' (i.e., "downstream") of the coding region and that are present on the mRNA are referred to as "3' untranslated sequences." The term "gene" encompasses both cDNA and genomic forms of a gene. A genomic form of a genetic clone contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "polymerase chain reaction" ("PCR") refers to the methods described in U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified." In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications. With PCR, it is possible to amplify a single copy of a specific target sequence in genomic DNA to a level detectable by the device and systems of the present invention.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "reverse transcriptase" and "RT-PCR" refer to a type of PCR where the starting material is mRNA. The starting mRNA is enzymatically converted to complementary DNA or "cDNA" using a reverse transcriptase enzyme. The cDNA is then used as a "template" for a "PCR" reaction.

As used herein, the term "real-time polymerase chain reaction" or "quantitative polymerase chain reaction" or "qPCR" refers to measuring changes in mRNA for determination of levels of specific DNA or RNA sequences in tissue samples. It is based on detection of a fluorescent signal produced proportionally during amplification of a PCR product. For example, Real-Time PCR measuring mRNA is done using a Taqman™ method of quantitative RT-PCR for measurement of changes in mRNA using the Perkin Elmer/Applied Biosystems Division 7700 Sequence Detector.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "sample template" refers to nucleic acid originating from a sample that is analyzed for the presence of "target" such as IL-22 produced in thymic epithelial cells. In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "sample" such as a "test sample" is used in its broadest sense. In one sense it can refer to an animal cell or tissue. In another sense, it is meant to include a specimen or culture obtained from any source, in particular as a biological sample. Biological samples may be obtained from animals (including humans) and encompass fluids, solids, gases, tissues, cells, and bones.

As used herein, "cells" refer to the structural unit of an organism consisting of a nucleus and organelles surrounded by a semipermeable cell membrane. It is not intended to be limited to live or functioning cells. In preferred embodiments, the invention relates to materials that contain, incorporate, attach, or bind stem cells, hematopoietic stem cells, endothelial cells, adipocytes, smooth muscle cells, reticular cells, osteoblasts, stromal fibroblasts, osteocytes and even more preferably, bone marrow stromal cells and mesenchymal stem cells.

As used herein, the terms "culture media," and "cell culture media," refers to media that are suitable to support the growth of cells in vitro (i.e., cell cultures). It is not intended that the temu be limited to any particular cell culture medium. For example, it is intended that the definition encompass outgrowth as well as maintenance media. Indeed, it is intended that the term encompass any culture medium suitable for the growth of the cell cultures of interest.

As used herein, the term "cell type," refers to any cell, regardless of its source or characteristics.

As used herein, the term "cell line," refers to cells that are cultured in vitro, including primary cell lines, finite cell lines, continuous cell lines, and transformed cell lines.

As used herein, the term "primary isolation" refers to the process of obtaining cells directly from a sample. Thus, primary isolation of cells, such as cells isolated from mice used for flow cytometry analysis, involves such processes as removing tissue from a subject, such as a thymus, bone marrow sample, etc. followed by digestion in an enzyme, for example, dispase. Primary isolation may be accomplished using solid or semi-solid agar media, or in liquid.

As used herein, the term "isolation" refers to any cultivation of cells, whether it be primary isolation or any subsequent cultivation, including "passage" or "transfer" of stock cultures of cells for maintenance and/or use.

As used herein, the term "portion" when used in reference to a population of cells (as in "a portion of TECs" or "a portion of bone marrow cells") refers to at least one cell of that population up to 99% of those cells. For example, where contacting results in at least a "portion" of said cell population, it should be clear that portion is with reference to a population.

As used herein, "polypeptide" or "protein" refers to an amino acid, amino acid sequence, oligopeptide, peptide, or protein or portions thereof whether naturally occurring or synthetic.

As used herein, the term "contacting" or "treating" cells with a compound, such as a cytokine, or cytokine composition refers to placing the cytokine or stain in a location that will allow it to touch the cell in order to produce "contacted" or "treated" cells. The contacting may be accomplished using any suitable method. For example, in one embodiment, contacting is by adding the cytokine, or cytokine composition to a tube of cells. Contacting may also be accomplished by adding the cytokine, or cytokine composition to cells in a microtiter plate. Contacting may also be accomplished by adding the cytokine, or cytokine composition to a culture of the cells. It is not meant to limit how the cytokine, or cytokine composition contacts the cells. In one embodiment, contacting may be accomplished by administration of cytokine, or cytokine composition to an animal in vivo.

The term "TBI" refers to "total body irradiation" as described herein.

As used herein, "lymphoid" in reference to a cell refers to those of the lymphoid lineage such as T cells, B cells and NKT (natural killer T) cells.

As used herein, "myeloid" in reference to a cell refers to those cells of a myeloid lineage such as macrophages (and monocytes), granulocytes (including neutrophils, eosinophils and basophils).

BRIEF DESCRIPTIONS OF THE DRAWINGS

FIG. 1: Exemplary demonstration of changes in lymphocyte populations resulting from a lack of IL-22 during development. Thymuses from WT and IL-22$^{-/-}$ animals were analyzed by flow cytometry and compared, by composition of subsets, within both hematopoietic and stromal compartments after digestion of tissue into a single cell population. A) Exemplary total thymic cellularity and the total number of CD4$^+$ CD8$^+$ DP (double positive), CD4$^+$ SP (single positive) TCRβ$^+$ or CD8$^+$ SP TCRβ$^+$ thymocytes. Concatenated flow cytometric plots of CD4 vs CD8 in samples displayed. B) Exemplary concatenated flow cytometry plot detailing ratio of cTEC to mTEC. Gated on DAPI$^-$ CD45$^-$EpCAM$^+$ MHCII$^+$ cells. C) Exemplary frequency of cTEC and mTEC within the thymus of WT and IL-22$^{-/-}$ animals. D) Exemplary total number of cTEC, mTEC, Fibroblasts and endothelial cells in the thymus. Bar graphs represent mean±SEM of at least 5 independent observations. FACS plots are concatenated files of each of these individual samples. WT=light graphs; IL-22 KO (knock-out)=dark graphs.

Figures 1, 2:
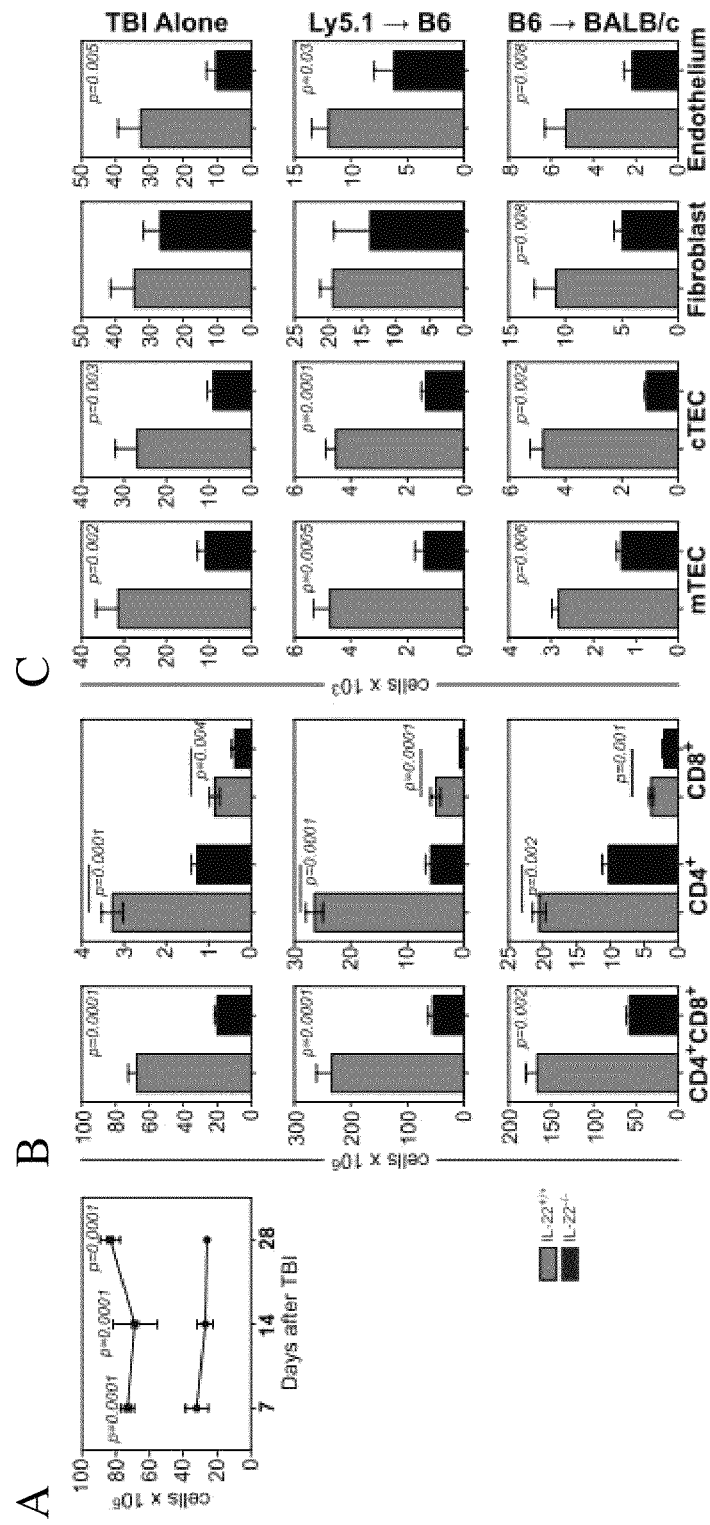

FIG. 2: Exemplary demonstration of IL-22 requirement for thymic regeneration following immunodepletion.

FIG. 2-1. A) Total number of cells in the thymus of WT B6 or IL-22$^{-/-}$ B6 animals 7, 14 or 28 days after sublethal (1×550 cGy) irradiation. B) Total number of CD4$^+$CD8$^+$, TCRβ$^+$ CD4$^+$ or TCRβ$^+$CD8$^+$ thymocyte subsets at day 28 in three models of immune depletion. The models examined were: TBI-alone (1×550 cGy in WT or IL-22$^{-/-}$ B6 animals); syngeneic-BMT (2×550 cGy+5×10$^6$ Ly5.1 BM donor cells transplanted into WT or IL-22$^{-/-}$ B6 recipients); or allogeneic-BMT (2×550 cGy+5×10$^6$ TCD B6 BM donor cells transplanted into WT or IL-22$^{-/-}$ BALB/c recipients). C) Total number of thymic stromal cells (Fibroblasts, Endothelium, mTECs and cTECs) in the aforementioned models of immune depletion at 28 days after treatment.

FIG. 2-2. Exemplary results are shown in Table 1.

Figure 3:
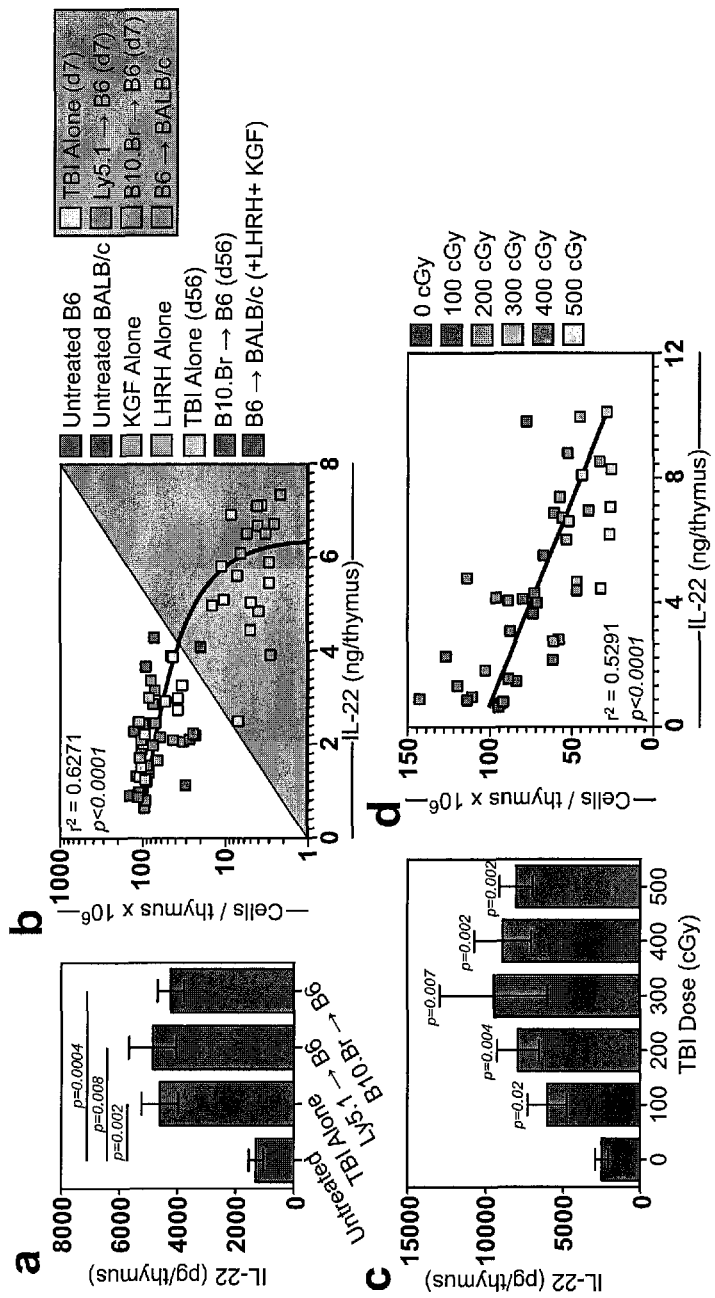
Figure 3:
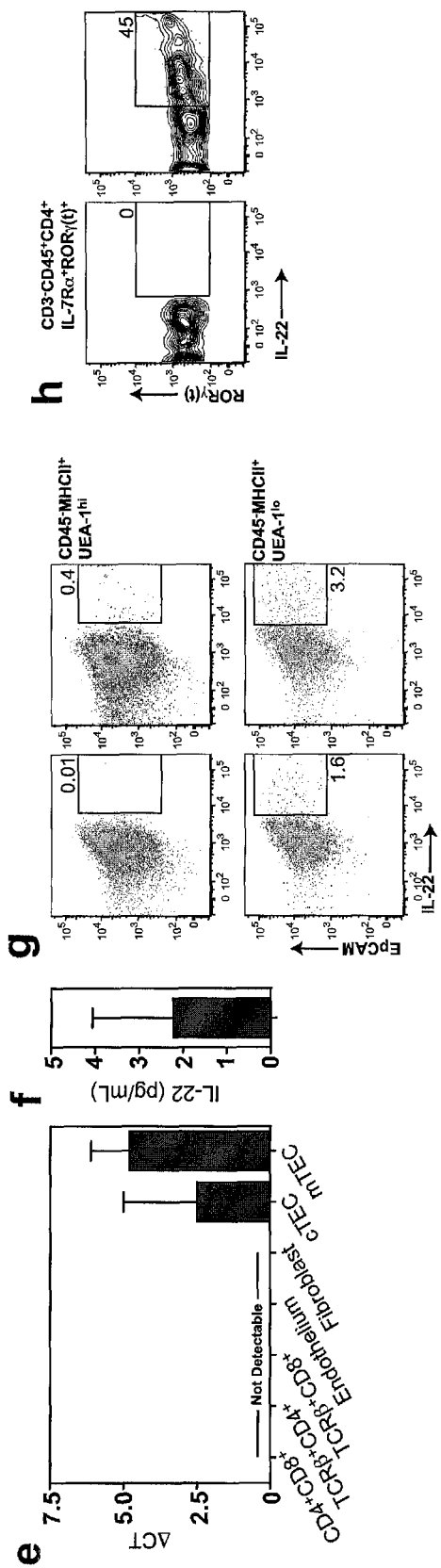

FIG. 3: Exemplary demonstration of IL-22 produced as a response to thymic damage. IL-22 was measured by ELISA in animals untreated or 7 days after several treatments: irradiation alone (550 cGy), syngeneic-BMT (2×550 cGy+5×10$^6$ Ly5.1 BMC) and allogeneic-BMT (2×550 cGy+5×10$^6$ TCD B6 BMC). a) Absolute levels of IL-22 were measured in the thymus for three models of immune depletion. The models used were untreated, 7 days after irradiation alone (550 cGy), syngeneic-BMT (2×550 cGy+5×10$^6$ Ly5.1 BMC) or allogeneic-BMT (2×550 cGy+5×10$^6$ TCD B6 BMC). b) Correlation between total thymic size and absolute levels of intrathymic IL-22. Data includes the aforementioned models of immune depletion. In addition: the therapeutic strategies of thymic regeneration keratinocyte growth factor (KGF) or leutenizing hormone releasing hormone analogue (LHRH-A) alone in in combination following allogeneic-HSCT (2×425 cGy+5×10$^6$ T cell depleted BM from B6 donors into BALB/c recipients); 56 days after TBI-alone or allogeneic-BMT (B10.Br into B6 recipients). c) Absolute levels of intrathymic IL-22 in different levels of thymic damage. IL-22 was measured 7 days after B6 animals were treated with 100, 200, 300, 400 or 500 cGy radiation. d) Correlation of thymic size and intrathymic IL-22 7 days after B6 animals were treated with 100, 200, 300, 400 or 500 cGy radiation. e) Relative change compared to housekeeping gene (HPRT) in different subsets of thymocytes or thymic stromal cells. f) Levels of IL-22 in cell cultures of the TEC line TE-71 cells (3 days of culture). g) Flow cytometry of mTECs and cTECs staining for IL-22 expression. h) IL-22 protein expression in intrathymic CD3$^-$CD45$^+$IL7Rα$^+$RORγ(t)$^+$ LTi-leike cells.

Figure 4:
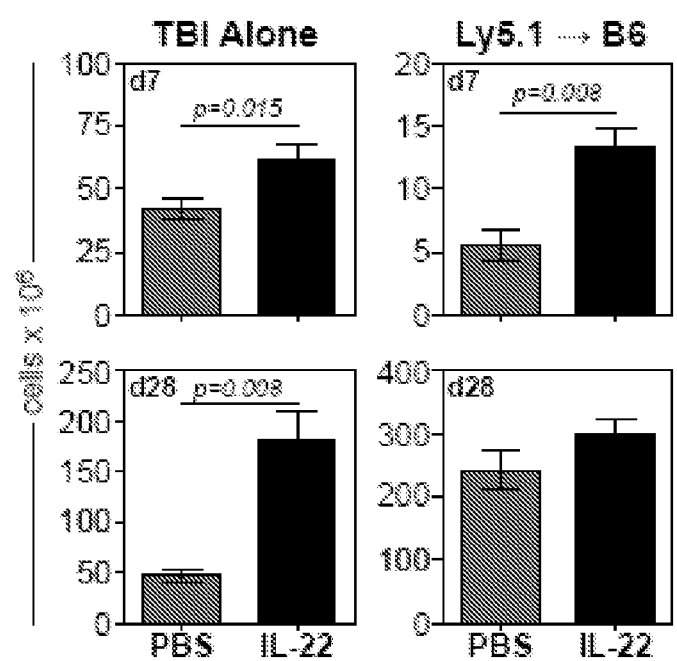

FIG. 4: Exemplary demonstration of administration of recombinant IL-22 which caused significantly enhanced thymic regeneration following insult/damage. Total thymic cellularity at days 7 and 28 in B6 animals treated with PBS or recombinant mouse IL-22 (4 µg/mouse/day for three days, −1, 0 and +1 days following irradiation). Models used were TBI-alone (1×550 cGy) or syngeneic-BMT (2×550 cGy+5×10$^6$ Ly5.1 BM cells).

Figure 5:
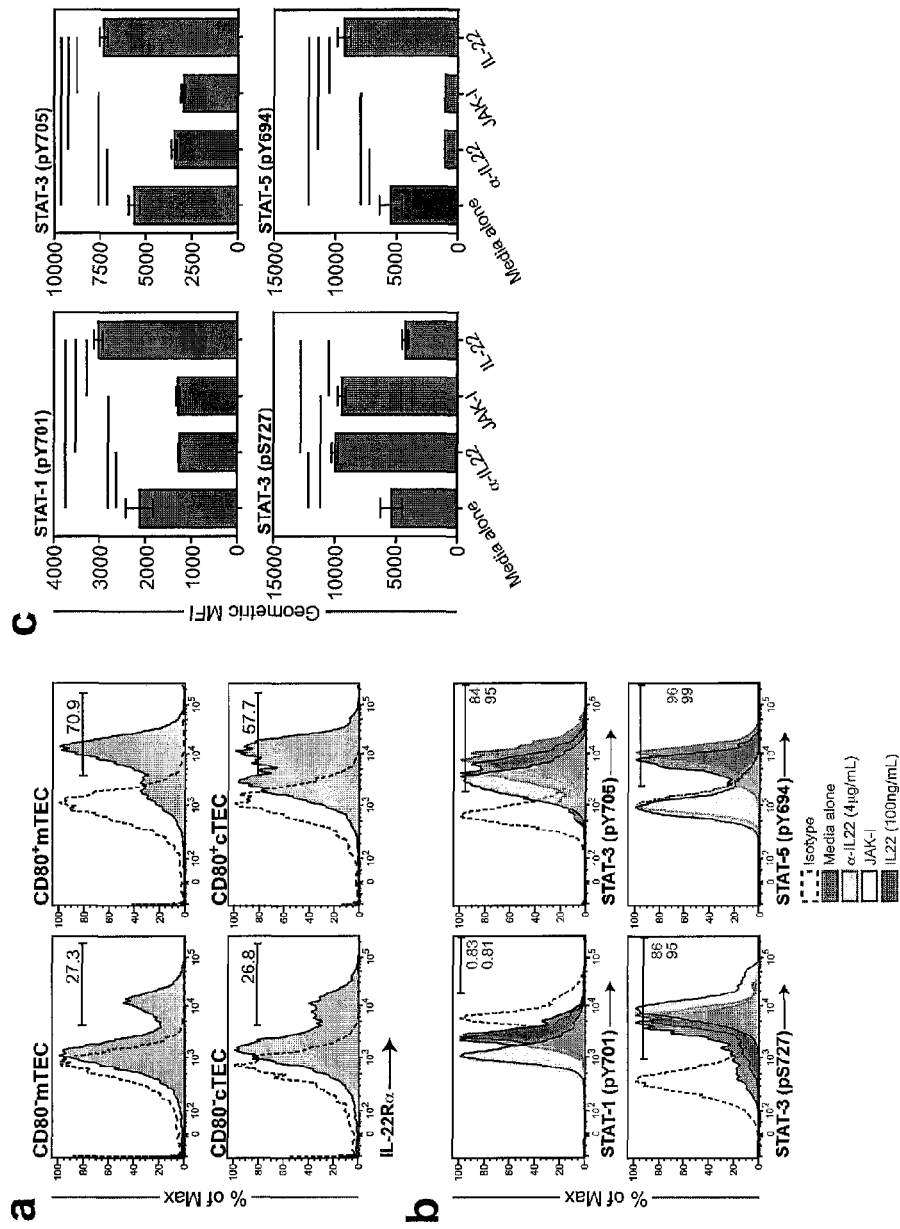

FIG. 5: Exemplary demonstration of IL-22 signaling through IL-22R which induced STAT signaling in TECS. a) IL-22R in mature CD80$^+$ and immature CD80$^-$ TECs. b) Flow cytometry plots outlining STAT signaling through the TEC line TE-71 treated with anti-IL-22, a pan JAK inhibitor (JAK-I) or IL-22 (100 ng). c) Mean fluorescence intensity of STAT signaling after treatment with anti-IL-22, a pan JAK inhibitor (JAK-I) or IL-22 (100 ng).

Figure 6:
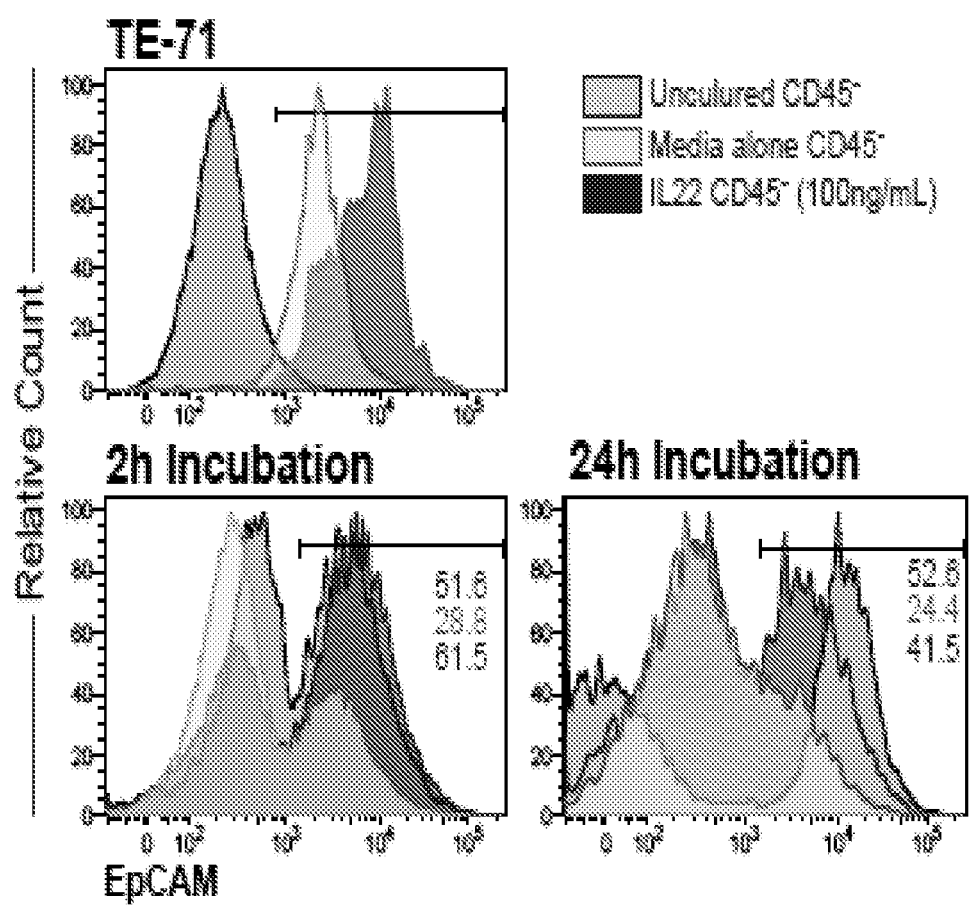

FIG. 6: Exemplary demonstration of IL-22 effects on thymic cell epithelial cell adhesion molecule expression. EpCAM (Epithelial cell adhesion molecule) expression in CD45-depleted cells uncultured (gray plot) or cultured for 2 or 24 hrs in the presence of PBS (red/yellow/light plot) or IL-22 (100 ng) (blue/dark plot).

Figure 7:
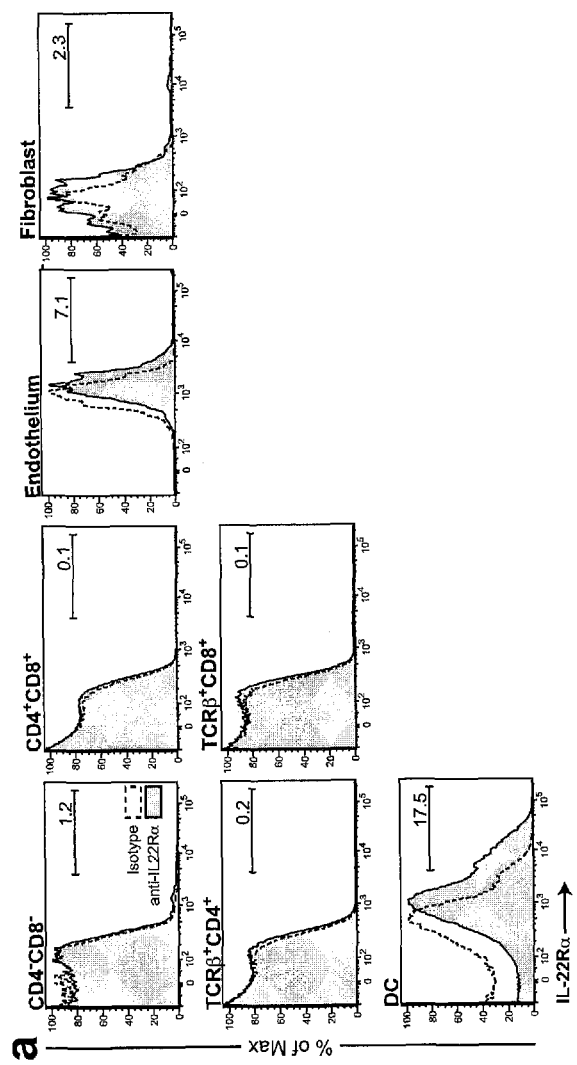

FIG. 7: Exemplary demonstration of lack of IL-22R expression in various thymocytes and thymic stromal cell subsets.

Figure 8:
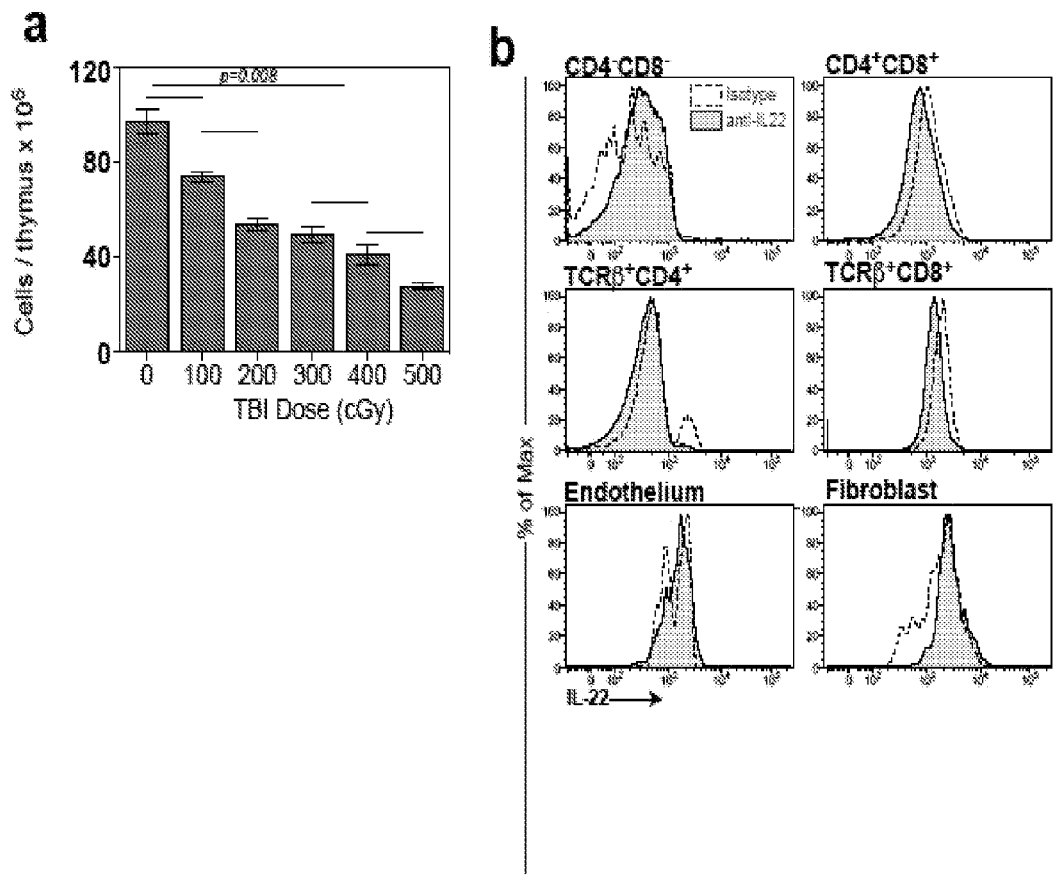

FIG. 8: Exemplary demonstration of thymic size and IL-22 production. a) Total thymic cellularity at day 7 in animals treated with doses of radiation from 100-500 cGy. b) IL-22 expression in thymocytes and thymic stromal cells (gray curves).

Figure 9:
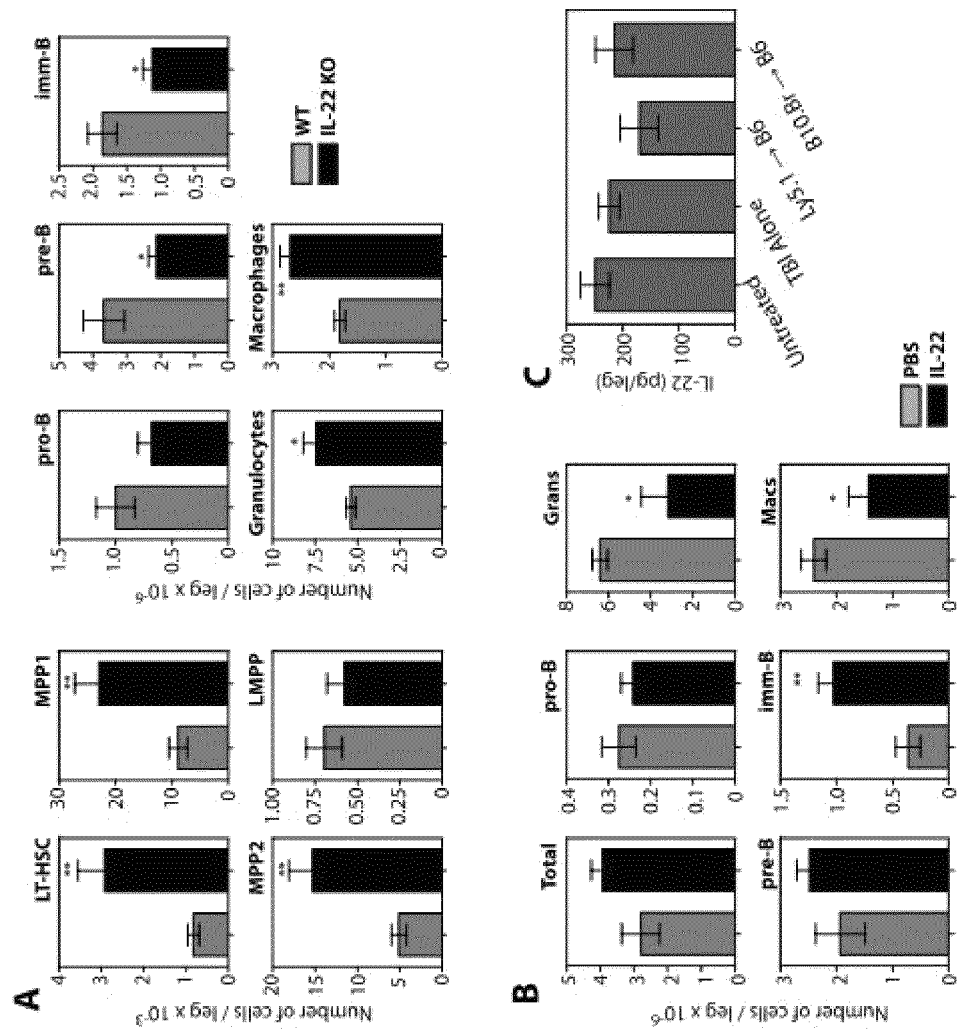

FIG. 9: Exemplary demonstration of IL-22 regulation of lymphopoiesis in the Bone Marrow. A: WT or IL-22$^{-/-}$ B6 mice were analyzed for numbers of developing B cells, myeloid cells and hematopoietic stem and progenitor cells. Phenotypes used are as follows: LT-HSC (long term-hematopoietic stem cell) Lin$^-$Sca1$^+$ckit$^+$(LSK) CD150$^+$CD48$^-$; MPP1, LSK CD150$^+$CD48$^+$; MPP2, LSK CD150$^-$CD48$^+$; LMPP (lymphoid-primed multipotent progenitor), LSK Flt3$^{hi}$CD150$^-$CD48$^+$; pro-B cells, B220$^+$CD43$^+$IgM$^-$; pre-B cells, B220$^+$CD19$^+$CD43$^-$IgM$^-$; imm(immature)-B cells, B220$^+$CD19$^+$CD43$^-$IgM$^+$; B: PBS or IL-22 (4 µg/mouse/day) treated animals were analyzed 7 days after sublethal TBI (1×550 cGy) for developing B cells, lymphoid progenitors and myeloid cells. C: Absolute levels of IL-22 were measured by ELISA in the BM of WT B6 mice 7 days after sublethal TBI alone (1×550 cGy), syngeneic (genetically identical) BMT (2×550 cGy TBI of B6 mice+5×10$^6$ Ly5.1 BM cells) or allogeneic (genetically different) BMT (2×550 cGy TBI of B6 mice+5×10$^6$ T cell depleted B10.Br BM cells). *, p<0.05; **, p<0.01.

Figure 10:
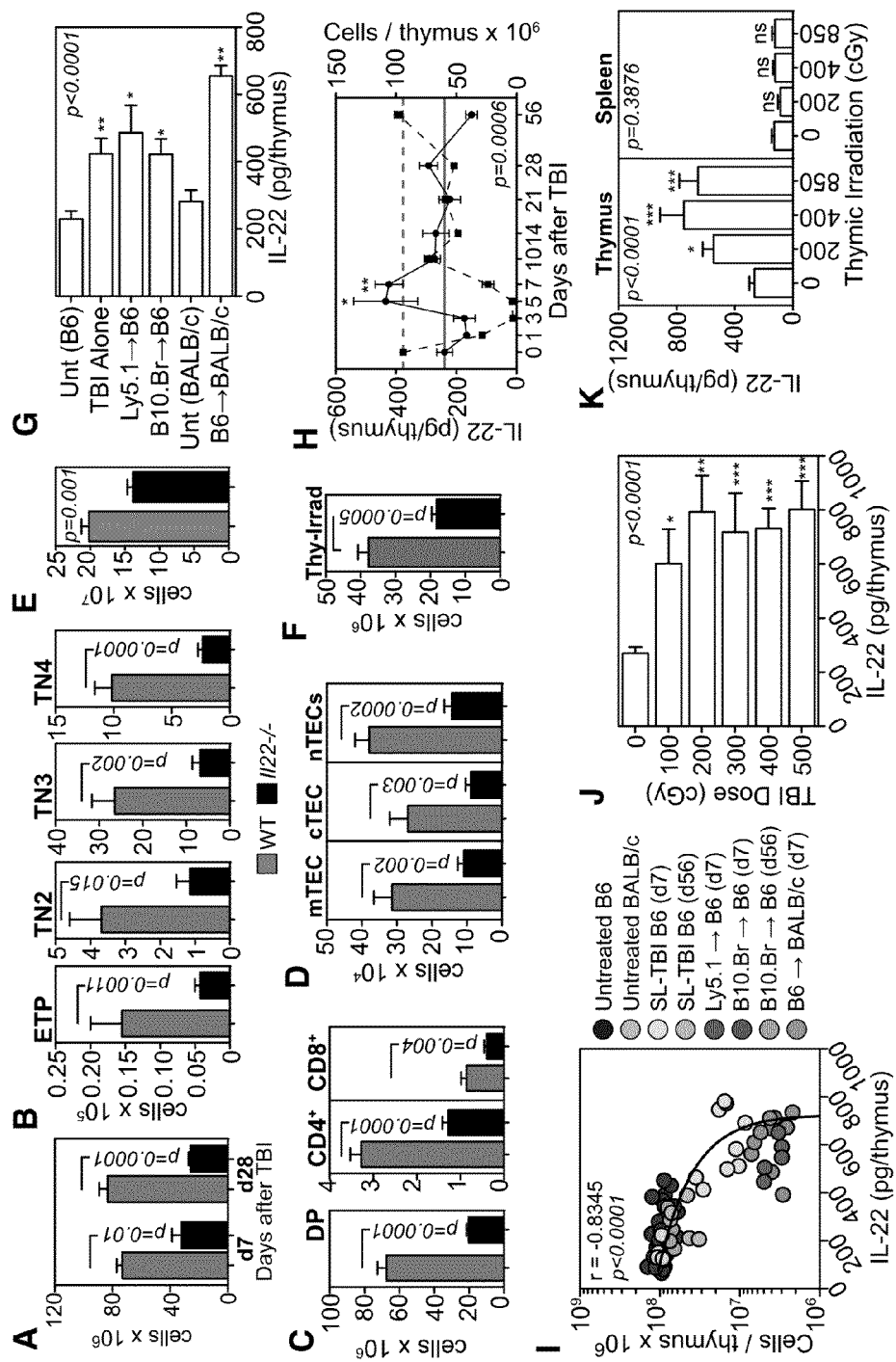

FIG. 10: Exemplary demonstration that IL-22 induced endogenous thymic regeneration and was upregulated upon thymic damage. A-D, WT (grey bars, n=11) and Il22$^{-/-}$ (black bars, n=11) C57Bl/6 mice were given SL-TBI (550 cGy) with no hematopoietic rescue and enzyme-digested thymus analyzed. Total thymic cellularity at days 7 and 28 after TBI (A), and developing thymocyte (B-C) and stromal cell subsets (D) 28 days after SL-TBI. E, Total thymus cellularity in WT (n=5) or Il22$^{-/-}$ (n=6) mice 98 days after SL-TBI. F, Total thymus cellularity seven days after targeted thymic-irradiation (850 cGy) of WT (n=10) or Il22$^{-/-}$ (n=7) mice. G, Absolute amounts of intrathymic IL-22 were measured by ELISA in untreated C57BL/6 (n=22), untreated BALB/c (n=5) or 7 days after SL-TBI without HSCT (550 cGy, n=15) or L-TBI and syngeneic HSCT (C57Bl/6 HSCs into congenic C57Bl/6 hosts, 2×550 cGy, n=10) or T cell depleted allogeneic-BMT (B10.BR HSCs into MHC-mismatched C57Bl/6 hosts, 2×550 cGy, n=10; or C57Bl/6 HSCs into MHC-mismatched BALB/c hosts, 2×425 cGy, n=5). H, Absolute amounts of IL-22 (solid circle) plotted with total thymic cellularity (dashed square) over time following SL-TBI (n=5-10/time point). Dashed and solid red lines represent mean cellularity and IL-22 amounts respectively at baseline. I, Spearman correlation between absolute amounts of intrathymic IL-22 and total thymic cellularity in various models of thymic insult. Bar graphs represent mean±SEM of at least 2-3 independent experiments.

Figure 11:
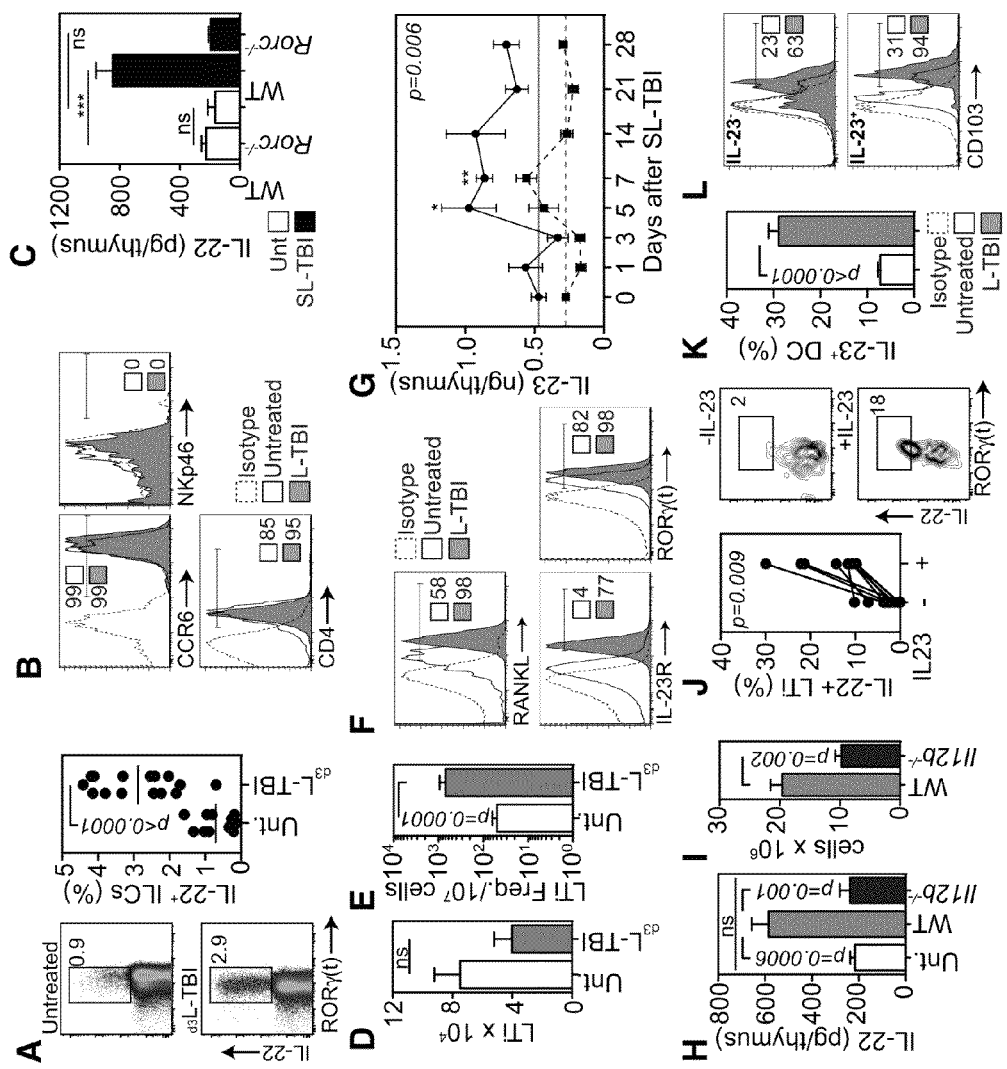

FIG. 11: Exemplary demonstration that IL-22 was produced by intrathymic ILCs under the control of IL-23. A-B, Enzyme-digested thymus from untreated (n=11) or three-days after L-TBI (n=15) was incubated with Brefeldin A (3 µg/ml) for 4 hours, but otherwise remained unstimulated. A, Intracellular expression of IL-22 and RORγ(t) by CD45$^+$IL-7Rα$^+$CD3$^-$CD8$^-$ tILCs in untreated or L-TBI animals. B, Expression of CCR6, NKp46 and CD4 on IL-22 producing tILCs. C, IL-22 levels measured by ELISA in thymus of untreated mice or 7 days after SL-TBI in WT or Rorc$^{-/-}$ mice. Absolute number (D) and frequency (E) of CD45$^+$IL-7Rα$^+$CD3$^-$CD8$^-$CD4$^+$RORγ(t) LTi in untreated mice (n=25) or 3 days after L-TBI (n=10). F, Expression of RANK ligand (RANKL), IL-23R and RORγ(t) in LTi from untreated mice or 3 days after L-TBI. G, C57Bl/6 mice were given SL-TBI (550 cGy) and absolute levels of IL-23 (solid circle) were measured by ELISA at days 1, 3, 5, 7, 10, 14 and 21 (n=5/time point). Compared with IL-22 kinetics (dashed square) taken from FIG. 1H. H-I, Absolute IL-22 levels measured by ELISA (G) and total thymic cellularity (H) in untreated mice (n=11) or 7 days after SL-TBI in WT (n=10) or Il12b$^{-/-}$ (n=8) animals. J, Untreated WT thymus was enzyme-digested and incubated+/−IL-23 (60 ng/ml) for 4 hours. After 1 hour of IL-23 incubation, Brefeldin A was added to all wells. IL-22 expression was examined in CD45$^+$CD3$^-$CD8$^-$ CD4$^+$IL7Rα$^+$RORγ(t)$^+$ LTi. K, Untreated (n=10) or 3 days after L-TBI (n=10) thymus cells were incubated for 4 hours in Monensin (2 µM), but otherwise remained unstimulated. Intracellular IL-23 expression in thymic DCs (CD45$^+$CD11c$^+$MHCII$^+$) was measured. L, Expression of CD103 on IL-23- and IL-23+ thymic DCs in untreated and L-TBI mice. Bar graphs represent mean±SEM of 2-3 independent experiments. FACS plots were generated by concatenation of at least 5 individual observations from one of at least 2 independent experiments.

Figure 12:
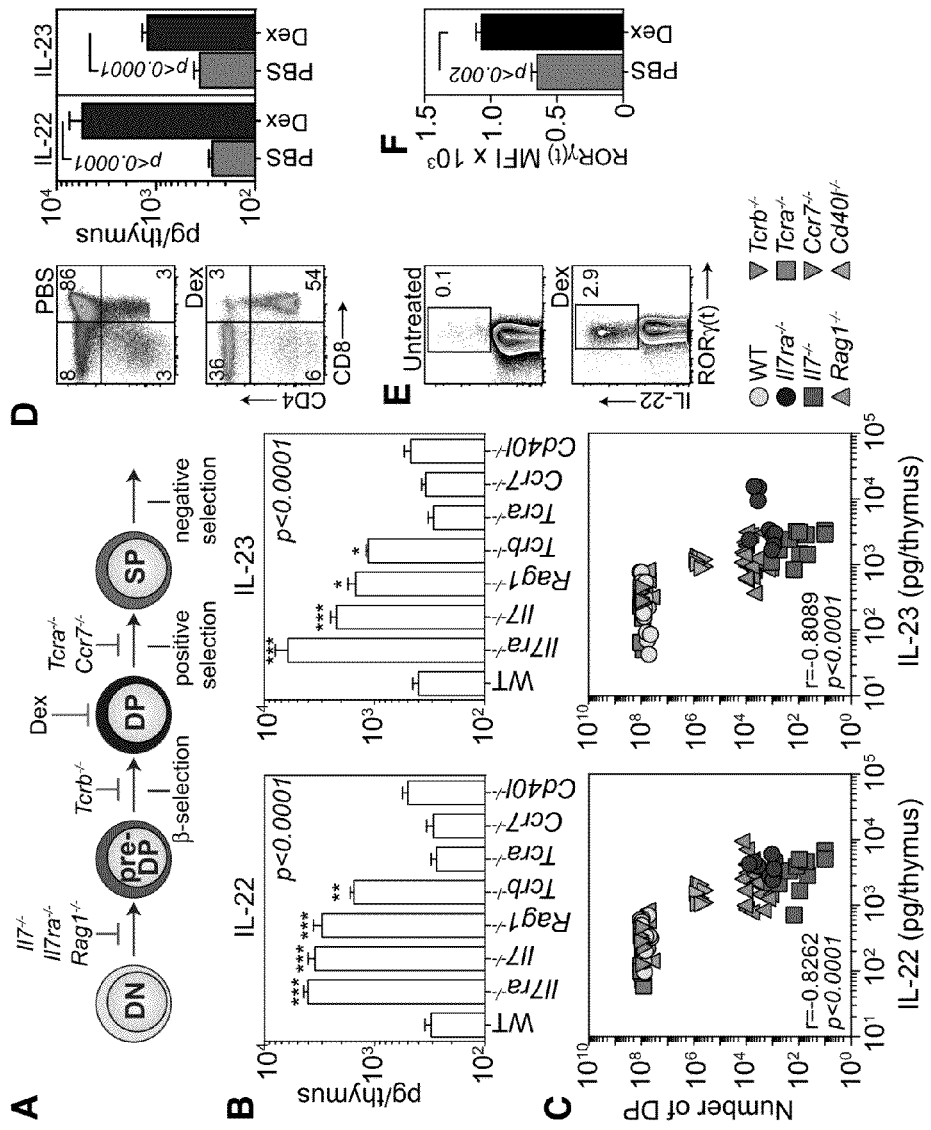

FIG. 12: Exemplary demonstration that absence of CD4$^+$CD8$^+$ double positive thymocytes triggers the upregulation of IL-23 and IL-22. A-C, Mutant mouse strains with blocks at different stages of T cell development were assessed for their production of IL-22 and IL-23. A, Schematic of T cell developmental stage blocked in various mutant strains/methods used. B, Absolute IL-22 and IL-23 at baseline in thymus of untreated WT (n=15), Il7Ra$^{-/-}$ (n=9), Il7$^{-/-}$ (n=11), Rag1$^{-/-}$ (n=22), Tcrb$^{-/-}$ (n=10), Tcra$^{-/-}$ (n=18), Ccr7$^{-/-}$ (n=6) and Cd40l$^{-/-}$ (n=10) mice. Statistical comparisons were made with the Kruskal-Wallis test with post-test comparison to WT controls. C, Spearman correlation between number of DP thymocytes and amounts of IL-22 or IL-23 in various mutant mouse strains. D-F, C57Bl/6 mice were treated with PBS (n=10) or dexamethasone (Dex) (20 mg/kg, n=11). D, Thymocyte profiles and absolute amounts of thymus IL-22 and IL-23 were assessed 5 days after treatment. E, Freshly isolated LTi from untreated WT (n=12) or Dex-treated (n=13) mice were analyzed for intracellular IL-22 with no incubation period. F, Mean Fluorescence Intensity (MFI) of RORγ(t) in LTi isolated from untreated or Dex-treated mice. Bar graphs represent mean±SEM and all data is generated from 2-3 independent experiments. FACS plots were generated by concatenation of at least 5 individual observations from one of at least 2 independent experiments.

Figure 13:
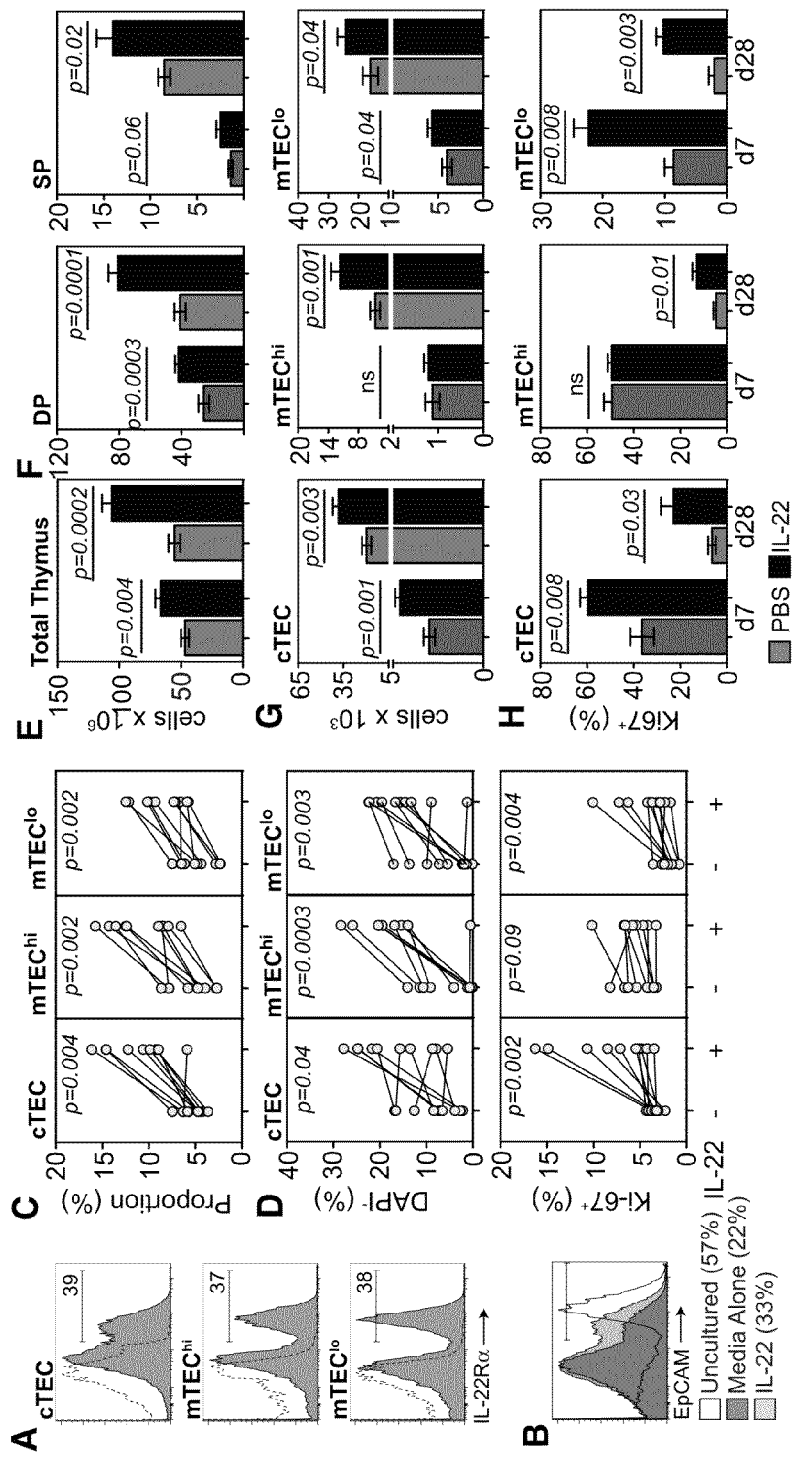

FIG. 13: Exemplary demonstration that exogenous administration of recombinant murine IL-22 enhanced thymopoiesis by promoting the proliferation and viability of TECs. A, WT thymus was enzyme-digested and enriched for CD45− cells. Expression of IL-22Rα on cTECs (UEA-1$^{lo}$), mTEC$^{lo}$ (UEA-1$^{hi}$MHCII$^{lo}$) and mTEC$^{hi}$ (UEA-1$^{hi}$MHCII$^{hi}$). All populations gated on CD45−EpCAM+. B-D, CD45− or MHC-II+ enriched thymus cells were incubated for 24 hours+/−IL-22 (100 ng/ml). B, Expression of EpCAM in uncultured CD45− cells (n=5) and in CD45− cells incubated for 24 hours with IL-22 (n=10) or media alone (n=10). C, Proportion of specific TEC subsets in CD45− cells incubated for 24 hours+/−IL-22. D, Expression of DAPI and Ki-67 on TEC subsets on MHCII-enriched thymus cells after 24 hours of incubation with IL-22 (n=10) or media alone (n=10). For in vitro experiments with enriched cells, each individual observation represents 3-4 pooled thymuses. E-H, C57Bl/6 mice were given SL-TBI (550 cGy), treated with PBS (grey bars, n=10) or IL-22 (black bars, 200 µg/kg/day, n=10-15) at days −1, 0 and +1 and assessed at days 7 and 28. Total thymus cellularity (E) and absolute number of thymocyte (F) and TEC subsets (G). H, Proportion of Ki-67 expressing cTECs, mTEC$^{lo}$ and mTEC$^{hi}$. Bar graphs represent mean±SEM of at least 2 independent experiments. FACS plots were generated by concatenation of at least 5 individual observations from one of at least 2 independent experiments.

Figure 14:
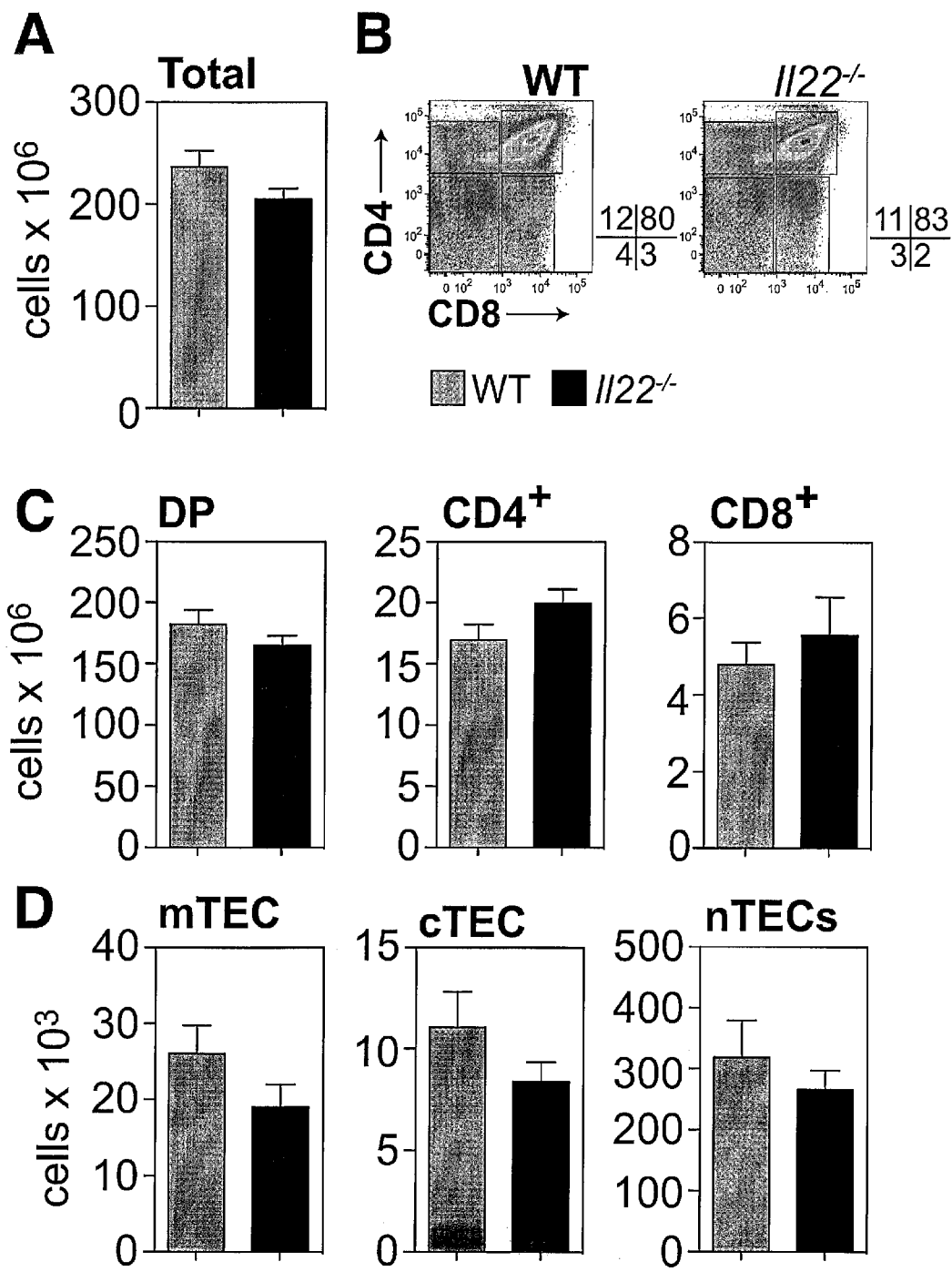

FIG. 14: Exemplary demonstration of an analysis of thymopoiesis at baseline in untreated C57Bl/6 WT (n=10) and Il22−/− (n=10) animals. A, Total thymic cellularity. B, Flow cytometric characterization of CD4 and CD8 expression. Plots are concatenated from 5 individual observations from one experiment. C, Total number of CD4+CD8+ double positive and TCRβCD4+ or TCRβCD8+ single positive thymocytes. D, Total number of thymic stromal cells including mTECs)(CD45−EpCAM+UEA-1$^{hi}$Ly51$^{lo}$), cTECs (CD45−EpCAM+UEA-1$^{lo}$Ly51$^{hi}$) and non-TEC stromal cells (CD45−EpCAM−). Bar graphs represent mean±SEM of 2 independent experiments.

Figure 15:
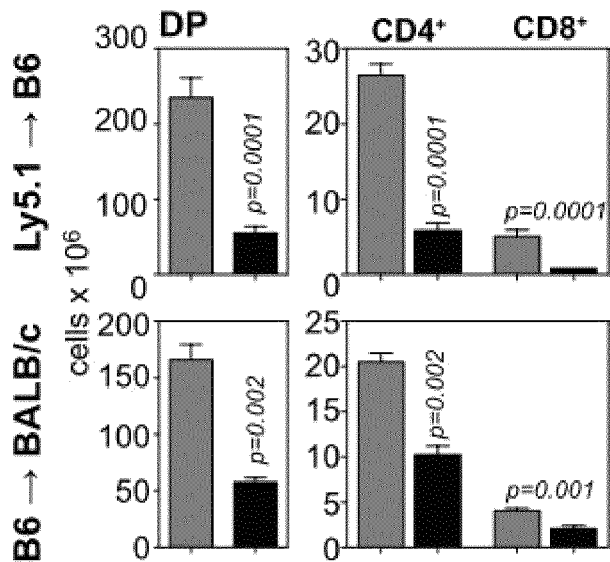
Figure 15:
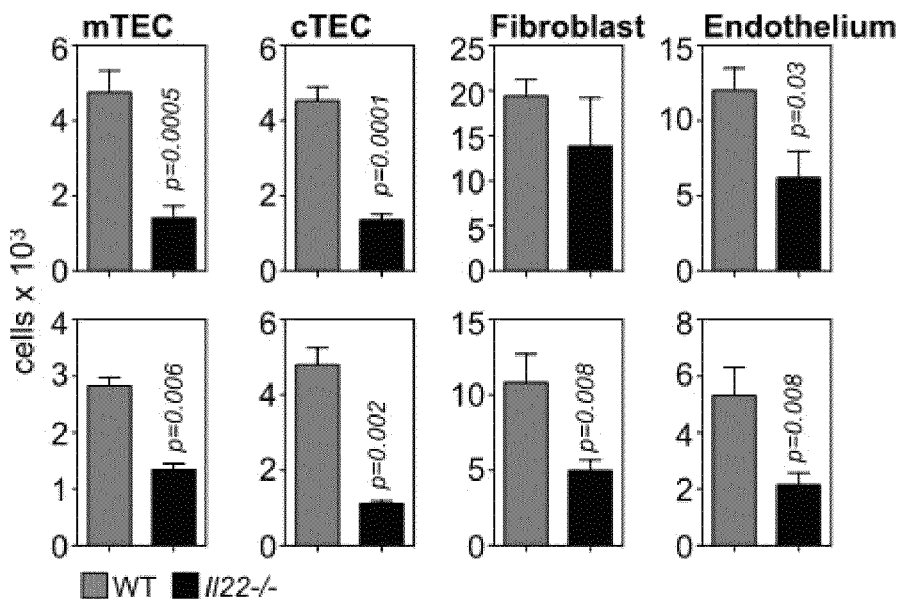

FIG. 15: Exemplary demonstration of IL-22 related affects after transplantation. A-B, Total number of thymocytes (A) and stromal cells (B) in syngeneic-HSCT (C57Bl/6 HSCs into WT or Il22$^{-/-}$ C57Bl/B6, 2×550 cGy, n=10/group) or T cell depleted allogeneic HSCT (C57Bl/6 HSCs into WT or Il22$^{-/-}$ BALB/c, 2×425 cGy, n=5/group) 28 days after transplant. Bar graphs represent mean±SEM in at least two independent experiments.

Figure 16:
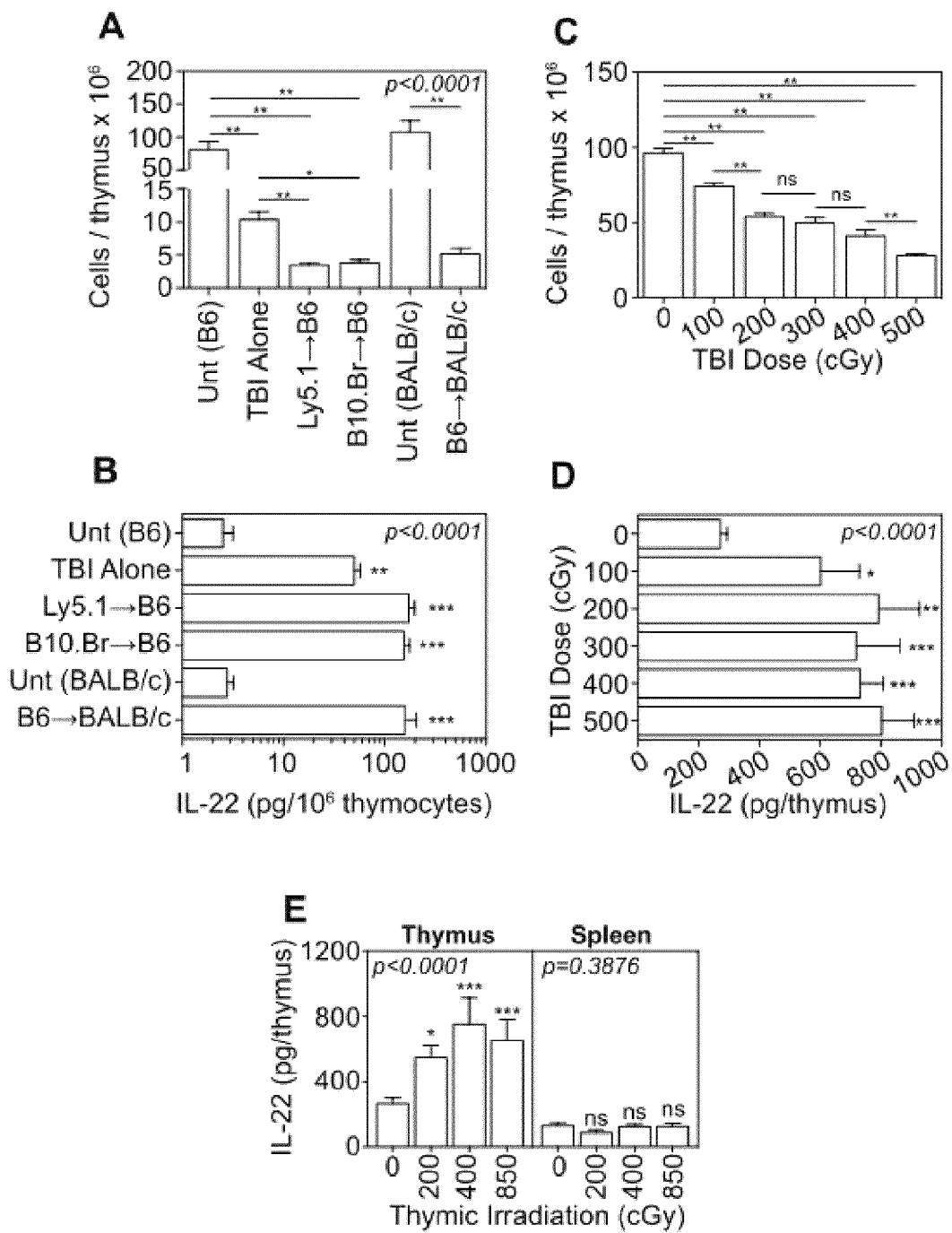

FIG. 16: Exemplary demonstration of IL-22 related affects of irradiated mice. A-B, Total thymic cellularity (A) and IL-22 on a per cell basis (B) in untreated C57BL/6 (n=22), untreated BALB/c (n=5) or 7 days after SL-TBI without BMT (550 cGy, n=10) or lethal TBI+syngeneic (C57BL/6 HSCs into congenic C57BL/6 hosts, 2×550 cGy, n=5) or T cell depleted allogeneic-BMT (B10.BR HSCs into MHC-mismatched C57Bl/6 hosts, 2×550 cGy, n=5; or C57Bl/6 HSCs into BALB/c hosts, 2×425 cGy, n=5). C, Total thymic cellularity in C57BL/6 mice given varying doses of SL-TBI and measured at day 7 (n=5-10/time point). Bar graphs represent mean±SEM of 1-2 independent experiments. D, Absolute amounts of IL-22 at 7 days after B6 animals were treated with 100, 200, 300, 400, 500 or 600 cGy TBI (n=5/TBI dose). E, Absolute amount of IL-22 in thymus and spleen of untreated (n=10) mice or at day 5 after 200 cGy (n=7), 400 cGy (n=8) or 850 cGy (n=20) doses of targeted thymic irradiation.

Figure 17:
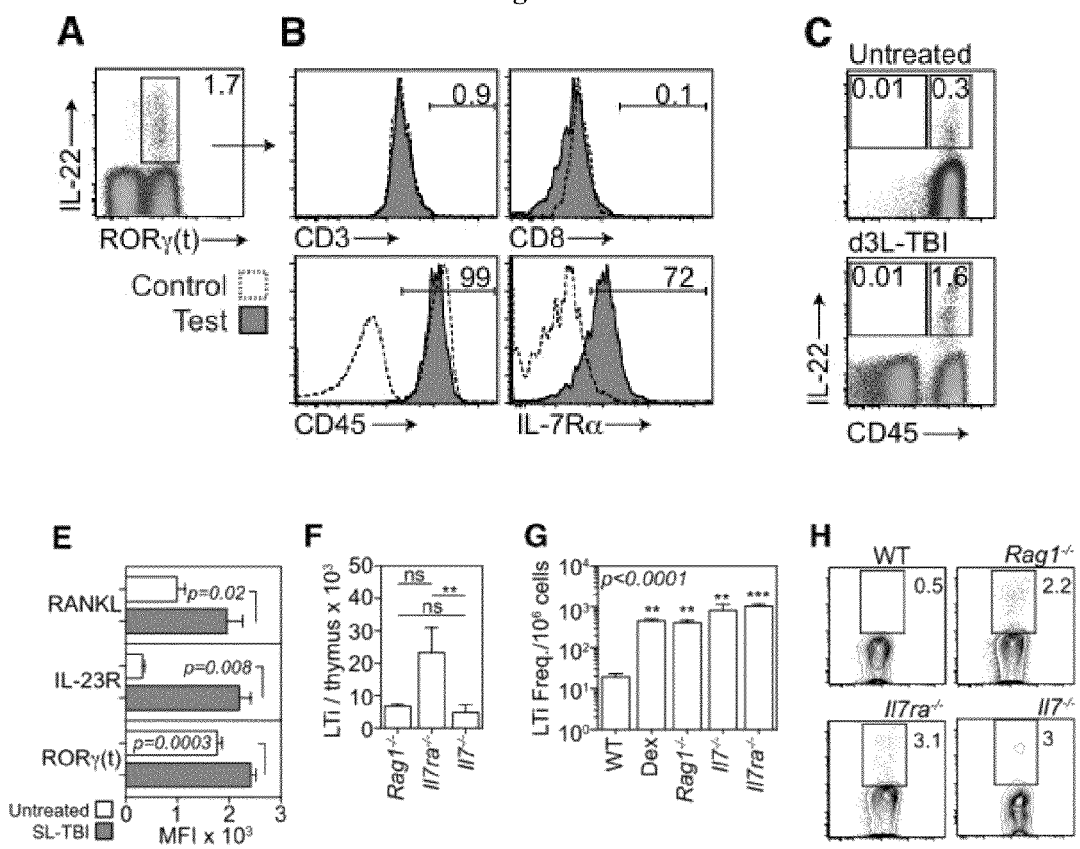

FIG. 17: Exemplary demonstration that no detectable IL-22 expression was found by CD3+ or CD45− populations. A-C, Thymus from WT mice were enzyme-digested at d3 after L-TBI and incubated for 4 hours in the presence of Brefeldin A. IL-22+ cells (A) were gated and then expression of CD3, CD8, CD45 and IL7Ra was examined (B). C, CD45 expression on thymus cells expressing IL-22. D, WT mice were given L-TBI and transplanted with 5×10$^6$ congenic BM cells. Three months after transplant, donor (CD45.2) and host (CD45.1) chimerism was assessed in CD3+CD8+SP8 thymocytes and thymic LTi. E, MFI of RANKL, IL-23R and RORγ(t) on thymic LTi in untreated and d3L-TBI mice. F, Number of LTi in the thymus of Rag1$^{-/-}$, Il7$^{-/-}$ and Il7ra$^{-/-}$ mice. G, Frequency of LTi in the thymus of Rag$^{-/-}$, Il7$^{-/-}$, Il7ra$^{-/-}$ and Dex-treated (day 5) mice. H, IL-22 expression in LTi cells isolated from digested thymus of untreated Rag1$^{-/-}$, Il7$^{-/-}$ or R7ra$^{-/-}$ mice with no incubation with Brefeldin A. Statistics in D represent Mann-Whitney comparisons while E-F represent Kruskal-Wallis test with post-test comparison to untreated WT controls.

Figure 18:
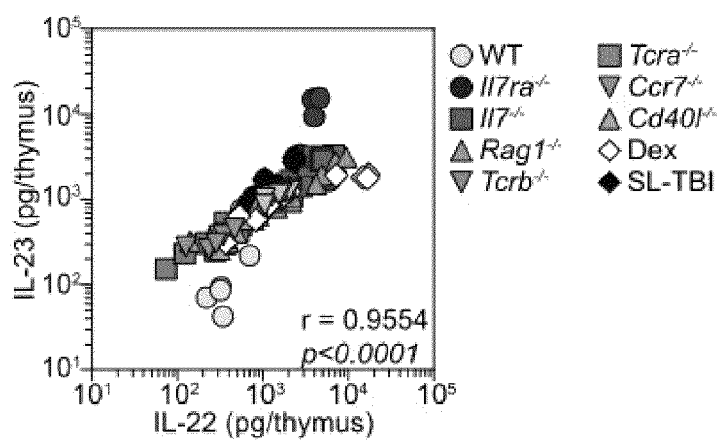

FIG. 18: Exemplary demonstration of Spearman correlation between absolute amounts of IL-22 and IL-23 in mutant mouse strains with defined blocks in T cell development as well as WT mice treated with dexamethasone (Dex) (day 5) or SL-TBI (day 7).

Figure 19:
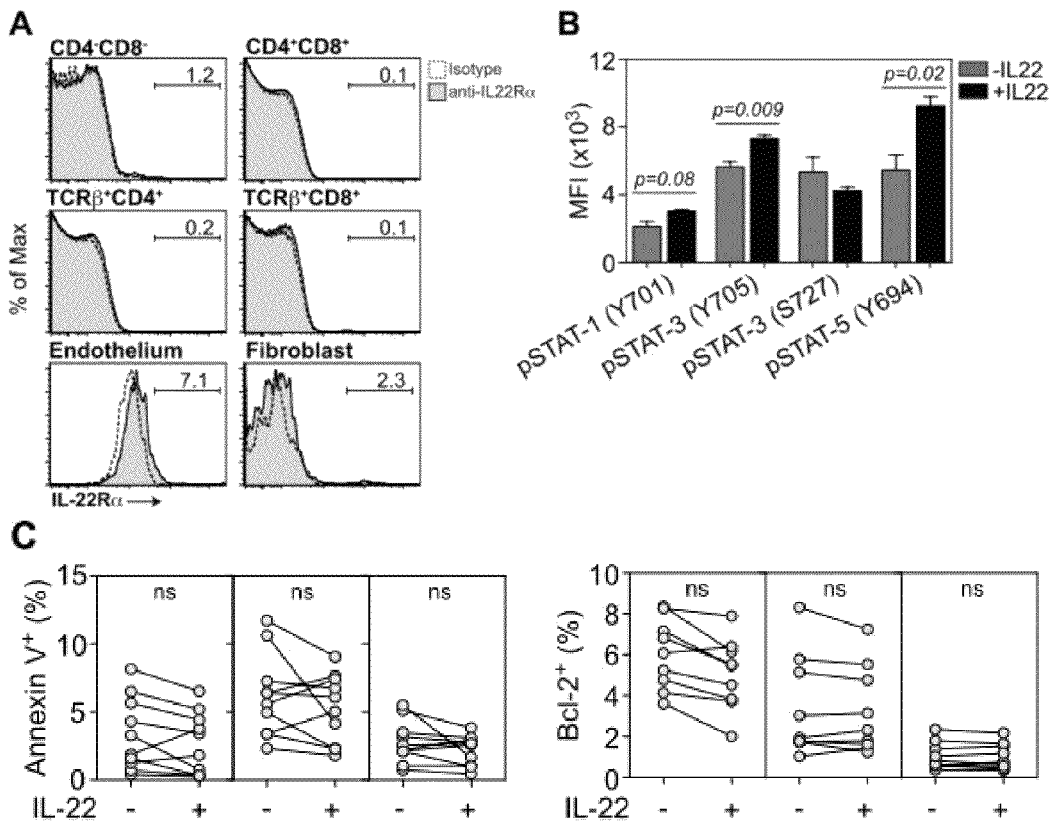

FIG. 19: Exemplary demonstration of IL-22R expression. A, IL-22Rα expression in various thymocyte and thymic stromal cell subsets. B, TE-71 TEC cell line was incubated with IL-22 (100 ng/ml) or media alone and STAT expression measured by flow cytometry after 1 hour. Mean Fluorescence Intensity (MFI) of pSTAT-1 (Y701), pSTAT-3 (Y705), pSTAT-3 (S727) and pSTAT-5 (Y694). Bar graphs represent mean±SEM, n=3/group. C, MHCII-enriched thymus cells were incubated for 24 hours in vitro with IL-22 (n=10) or media alone (n=10). Expression of Annexin V and Bcl-2 on specific TEC subsets.

Figure 20:
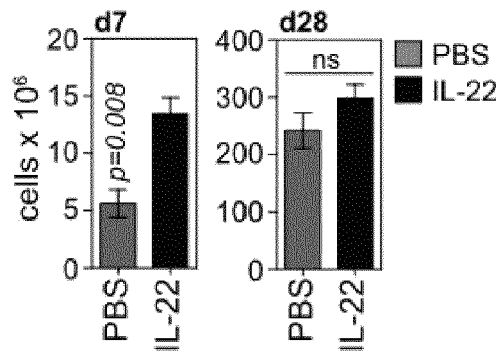

FIG. 20: Exemplary demonstration of IL-22 treatment when C57BL/6 mice were given L-TBI+syn-HSCT (2×550 cGy+5×10$^6$ Ly5.1+ BM cells). IL-22 was administered i.p. pen-transplant at days−1, 0 and +1. Total thymus cellularity at days 7 and 28 (n=5-10/group). Bar graphs represent mean±SEM and statistics represent Mann-Whitney comparisons.

Figure 21:
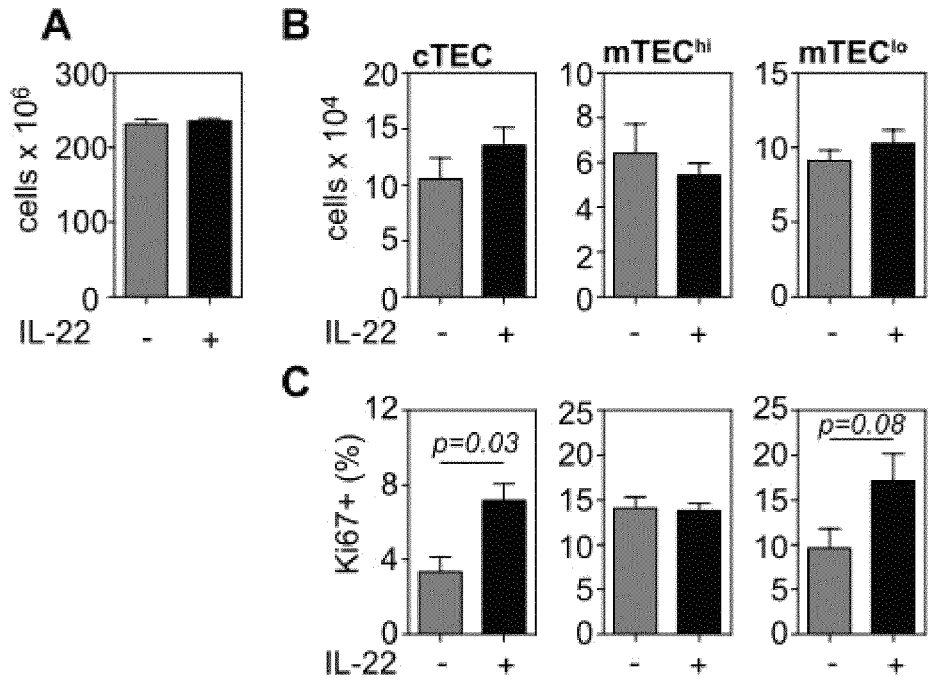

FIG. 21: Exemplary demonstration of IL-22 treatment that demonstrated a small increase in cTEC and mTEC$^{lo}$ proliferation. A-C, C57BL/6 mice were treated daily with PBS or IL-22 (200 µg/kg/day). Total thymic cellularity (A) and total number of cTECs, mTEC$^{hi}$ and mTEC$^{lo}$ (B) at day 7. C, Proportion of cTECs, mTEC$^{hi}$, mTEC$^{lo}$ expressing Ki-67. Bar graphs represent mean±SEM, n=5/group.

Figure 22:
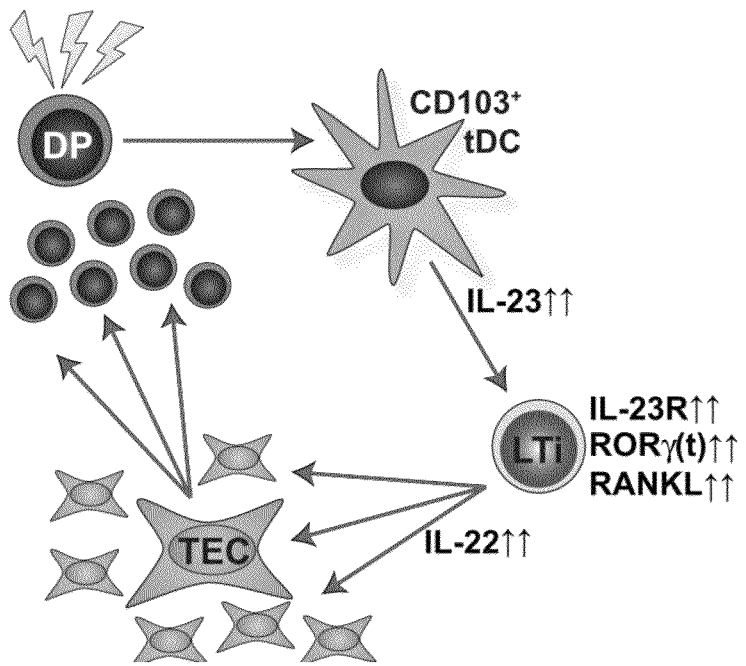

FIG. 22: Exemplary demonstration of IL-22 related enhanced thymopoiesis. Conceptual framework of endogenous regeneration following thymic injury. Depletion (or absence) of CD4+CD8+DP thymocytes triggers the upregulation of IL-23 production by thymic dendritic cells (DCs). This in turn leads to increased production of IL-22 by CD45+ IL7Rα+RORγ(t)+CCR6+NKp46− lymphoid tissue-inducer cells (LTi) that also upregulate their expression of RORγ(t), IL-23 receptor (IL-23R) and RANK ligand in response to thymic injury. IL-22 signals through thymic epithelial cells (TECs) and promotes their proliferation and survival. This cascade of cellular and molecular events ultimately leads to regeneration of the stromal microenvironment and, through thymic crosstalk, recovery of thymopoiesis and the DP pool.

Figure 23:
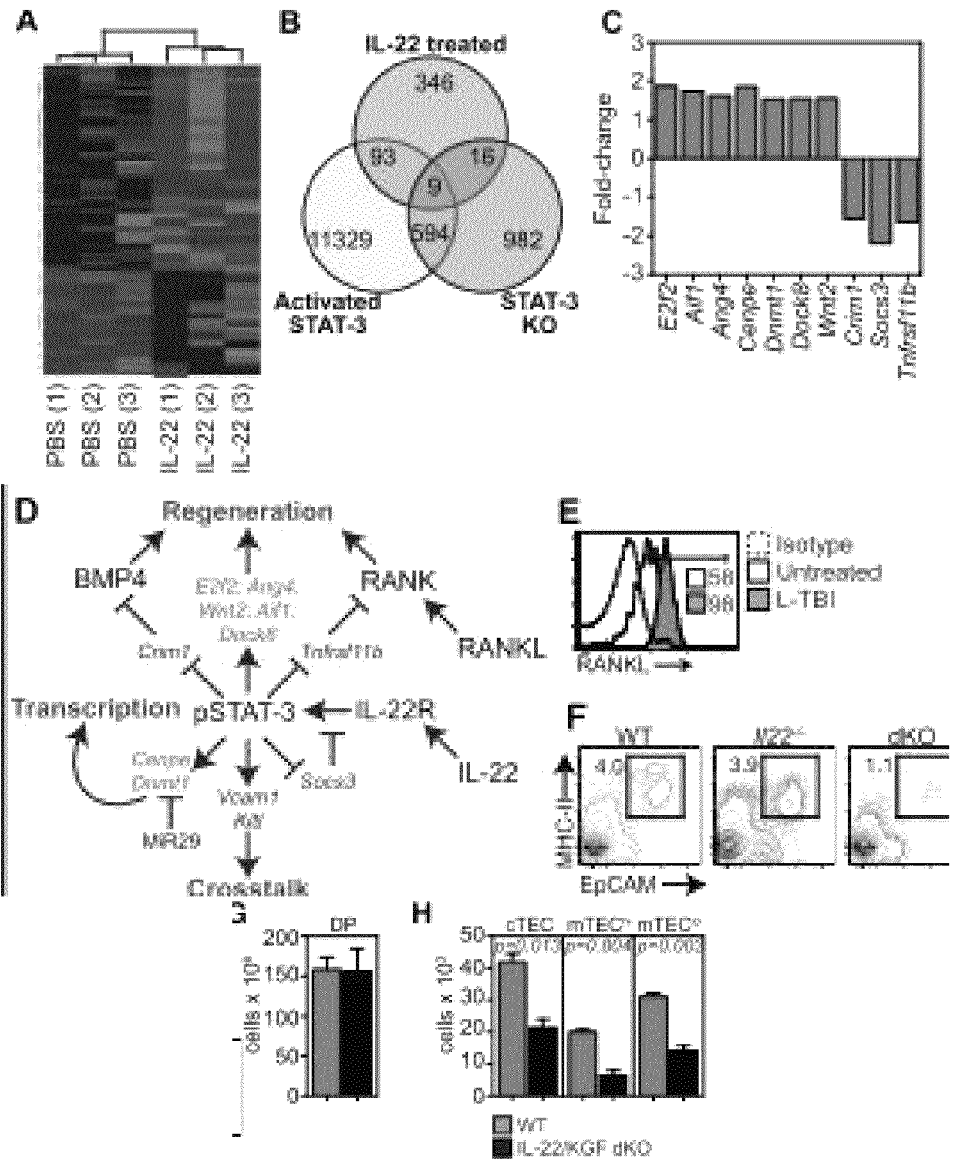

FIG. 23: Exemplary demonstration of gene expression after treatment of mice with IL-22. A, Unbiased cluster analysis of changed genes in PBS treated or IL-22 treated (200 mg/kg/day) mice given SL-TBI. B, Changed genes comparing IL-22 treated TECs, STAT-3 KO alveolar epithelium (GEO ID GDS3106) or activated STAT-3 in MEFs (GEO ID GSE2251).>1.3 fold change, p<0.05. C, Fold change of selected genes in CD45− cells isolated from mice given SL-TBI and treated with IL-22 or PBS. D, Relationship between genes identified as changed in TECs after treatment with IL-22. E, RANKL expression on LTi isolated from untreated or after TBI. F, TECs in WT, IL22−/−, or IL-22/KGF dKO mice. G-H, Total number of CD4+CD8+ double positive (DP) thymocytes (G) or TECs (H) in WT or IL-22/KGF dKO mice. Bar graphs represent mean±SEM.

Figure 24:
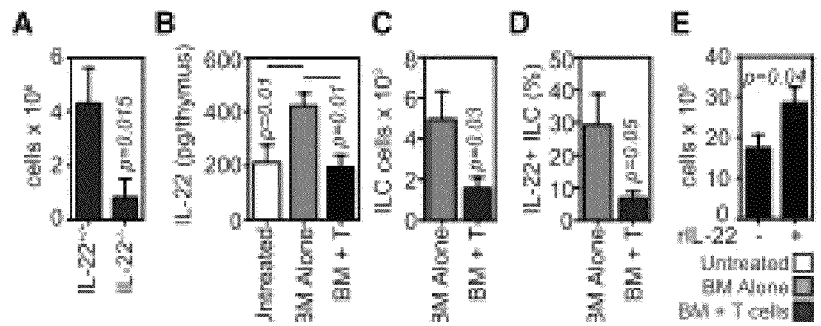

FIG. 24: Exemplary demonstration of IL-22 treatment after inducing thymic graft vs. host disease (GVHD). WT or IL-22 KO BALB/c mice were given L-TBI with T-cell depleted (TCD) B6 BM and B6 T cells to induce GVHD. A, Total thymus cells at 3 weeks after transplant. B, B6 mice were given L-TBI with TCD B10.BR BM with or without B10.BR T cells. Absolute levels of IL-22 were measured at day 7. C, ILC were enumerated by isolation from BALB/c mice 21 days after TBI with B6 BM alone or with the addition of B6 T cells to induce GVHD. D, ILCs isolated from BALB/c mice 21 days after TBI with B6 BM alone or with the addition of B6 T cells to induce GVHD were incubated in vitro with IL-23. Intracellular IL-22 expression was assessed in ILCs. E, B6 mice were given L-TBI with TCD LP BM alone (grey bars) or with LP T cells (black bars). Mice were also treated with PBS or rIL-22 (200 ug/kg/day) daily. Number of CD4+CD8+ thymocytes at 3 weeks after transplant.

Figure 25:
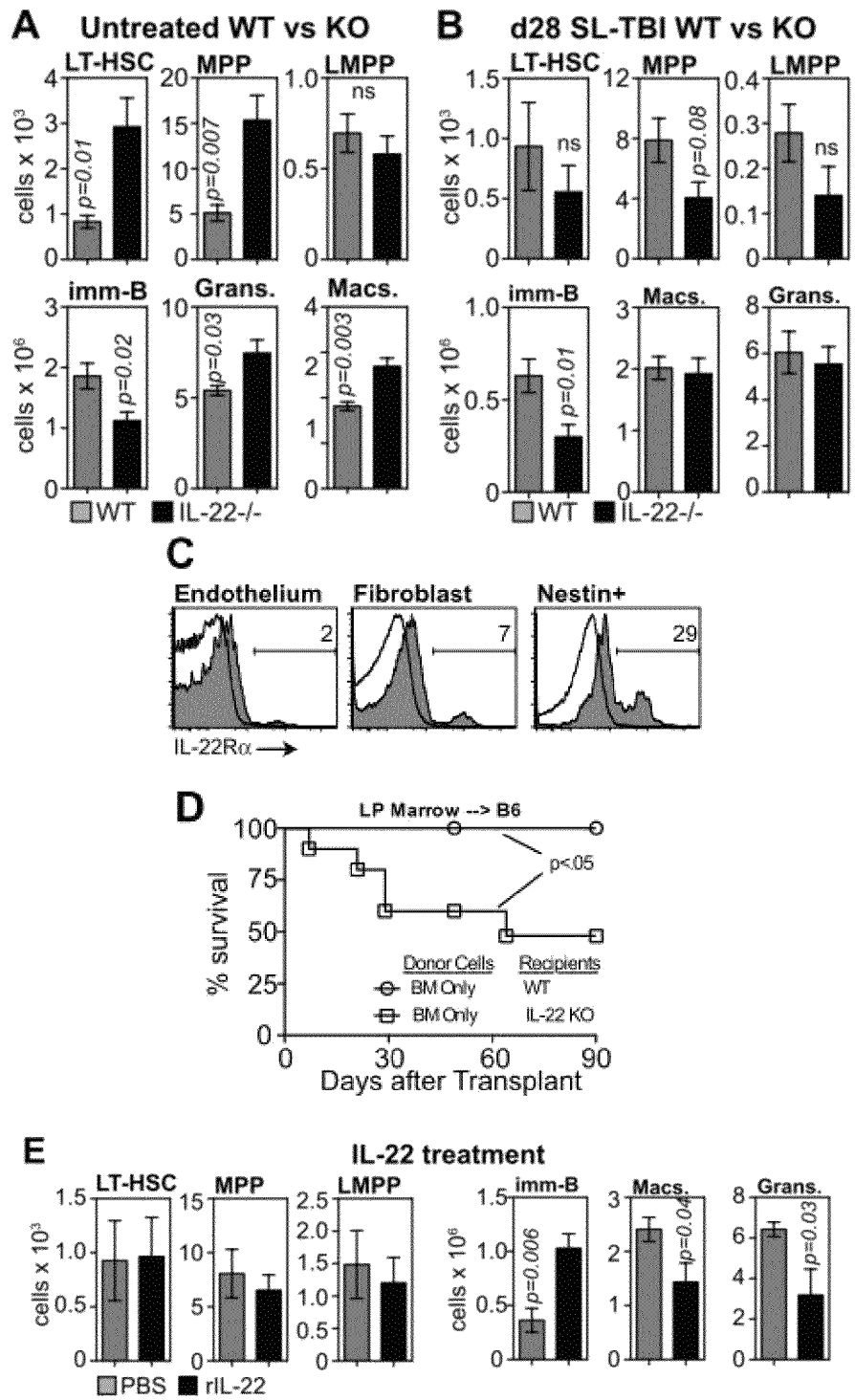

FIG. 25: Exemplary demonstration of IL-22 targeted Nestin+ cells in the Bone Marrow. A shows an exemplary comparison of untreated wild type mice (WT) vs. IL-22 knock out (KO) mice, Number of BM cells in untreated WT (n=5) and IL-22−/− (n=5) C57Bl/6 mice. B, shows an exemplary comparison of mice on day 28 (d28) of SL-TBI WT (n=5) vs. IL-22 KO (n=6) that were given SL-TBI (550 cGy) with no hematopoietic rescue and BM analyzed. C, BM of Nestin-GFP mice were examined for IL-22Rα expression on CD45−CD31+ Endothelium and CD45-PDGFRa+Fibroblasts. Nestin+PDGFRa+ cells (MSCs) were also examined. D, Lethally irradiated WT or IL-22−/− B6 mice transplanted only with T cell-depleted LP marrow. E, PBS (n=5) or recombinant IL-22 (n=5) was administered to mice at d−1, 0 and +1 (200 ug/kg/day) surrounding SL-TBI. BM was analyzed at day 7.

Figure 26:
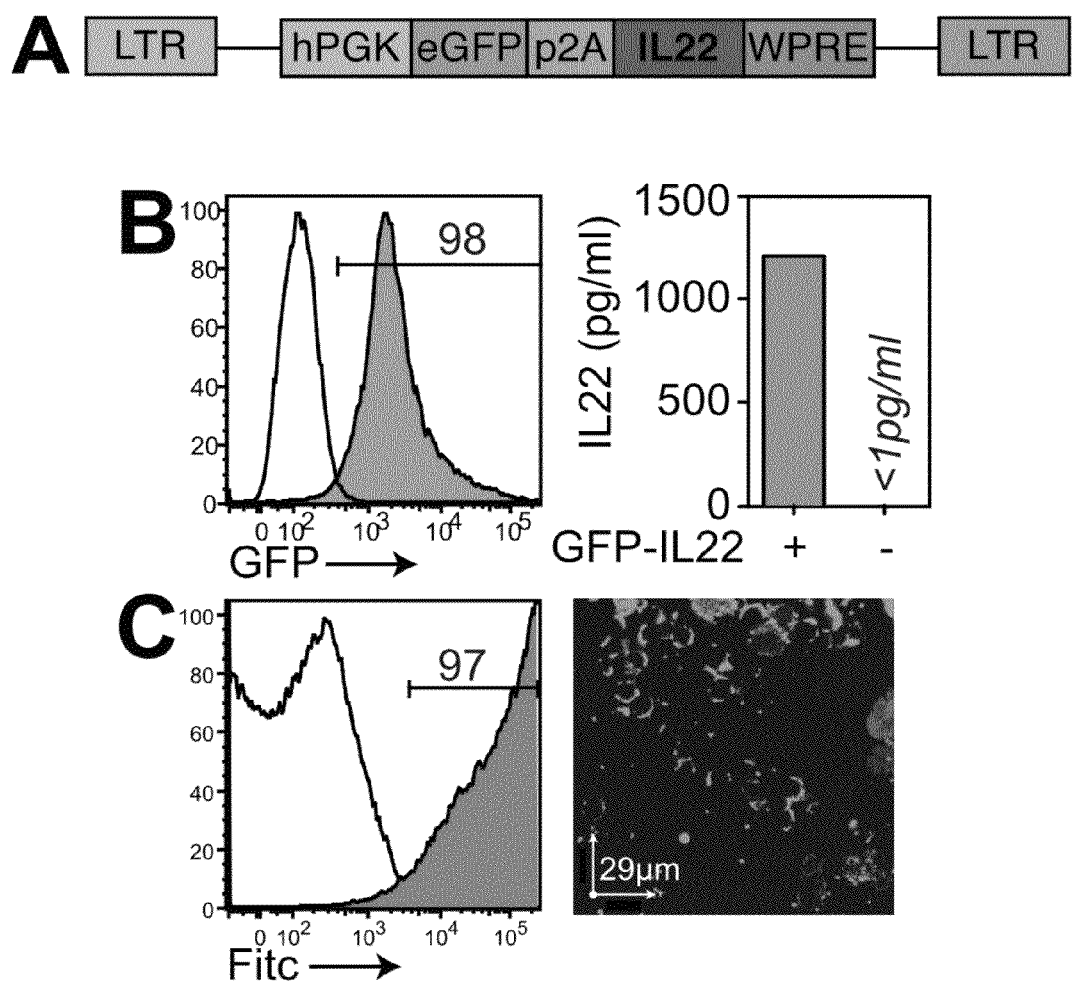

FIG. 26: Exemplary demonstration of strategies to administer IL-22 post-HSCT. (A-B) Lentiviral construct allows for constitutive IL-22 production and detection by GFP expression. A, IL-22-GFP construct. B, GFP expression in transfected vs. untransfected 293T cells after 72 hour culture. (C) nano particles were generated and loaded with Fitc-dextran. Flow cytometry and microscopy showing Fitc+ preT cells.

DESCRIPTION OF THE INVENTION

In one embodiment, the present invention provides methods and compositions for the use of IL-22 to promote thymic growth following thymic insult. In particularly preferred embodiments, the present invention provides methods of using therapeutic IL-22 compositions for treating patients with thymic atrophy and alterations in bone marrow derived white blood cells hematopoietic function, including cancer patients undergoing chemotherapy, patients exposed to radiation (i.e. cancer therapy, nuclear disaster, terrorist attack, etc.), patients with HIV infections/AIDS, patients with organ transplantation, aging patients, and the like. In a further embodiment, therapeutic IL-22 compositions are contemplated as a prophylactic to boost immune response when additional T-cell function is needed, i.e. to boost immune response during vaccination. Thus, IL-22 compositions of the present inventions are contemplated for use in vaccination methods.

Indeed, the present invention provides in one embodiment a new treatment comprising. IL-22 for restoring or altering immune functions, in particular by altering development of lymphoid and myeloid subsets in thymus and bone marrow. As discussed in greater detail below, in preferred embodiments, the methods provided by the present invention take advantage of the capacity for restoring (or rejuvenating) thymic and bone marrow function (including epithelial cell function) provided by administering IL-22. Also as discussed in greater detail below, in these preferred embodiments, restoration of white blood cell subsets (compartments) are used as a true measure of restoration of thymic function.

Thymic function is reduced from numerous causes including "age-related involution to atrophy as a consequence of malnutrition, infection or harmful influences, such as chemotherapy and radiation. The loss of regular thymus function significantly increases the risk for infections and cancer because of a restricted capacity for immune surveillance" (Hollander, et al., Current Opinion in Pharmacology 2010, 10:443-453, herein incorporated by reference).

While during the development of the present inventions, a lack of IL-22 during development was not found to be required for thymic development and function, it was found to contribute for post-natal thymic regeneration. This is possibly mediated through its actions on promoting cell survival, as a maturation signal, particularly for mTECs (medullary thymic epithelial cells) and contemplated to prevent apoptosis within TECs and promote proliferation of TECs. Further, as demonstrated herein, IL-22 signaled through the IL-22R on the surface of TECs, in particular on CD80+ mTECs and cTECs. This discovery was in apparent contrast to Wolk, et al., (Biology of interleukin-22, Semin Immunopathol (2010) 32:17-31, herein incorporated by reference) where the authors state that expression of the IL-22R1 chain determines whether a cell is an IL-22 target or not . . . using quantitative reverse transcriptase polymerase chain reaction, no expression of IL-22R1 was detected in bone marrow, blood mononuclear cells, thymus, or spleen (Wolk, et al., (2004) IL-22 increases the innate immunity of tissues. Immunity 21:241-254, herein incorporated by reference) or in a variety of isolated resting or activated primary immune cells including monocytes, B cells, T cells, NK cells, macrophages, and immature and mature DCs (Wolk, et al., J Immunol 168:5397-5402; J Leukoc Biol 83:1181-1193; Eur J Immunol 36:1309-1323; Immunity 21:241-254, herein incorporated by reference in their entirety). Further, a secreted ("soluble"), single-chain, high affinity IL-22 binding receptor named IL-22 binding protein (IL-22BP) has mRNA that was reported expressed in some human tissues including tissues thymus. However Wolk, et al., also reported that several studies had shown that IL-22BP binds to IL-22 and potently inhibits cellular IL-22 effects (Biology of interleukin-22, Semin Immunopathol (2010) 32:17-31, herein incorporated by reference).

Further adding to the evidence of the novel biological role of IL-22 in thymic regeneration, IL-22 levels were increased significantly when measured following thymic insult and correlated significantly with reduced thymic size. Moreover, once thymic renewal returned to untreated levels the level of IL-22 was stabilized. These findings demonstrate a novel endogenous mechanism of post-natal thymic regeneration.

IL-22 is one member of the IL-10 family of cytokines. It has multiple roles in inflammation and maintenance of epithelial barrier function, primarily in mucosal tissue. The role of IL-22 was not clearly defined since IL-22 shows different and sometimes-opposite effects depending upon the experimental conditions. However as described herein, the inventors discovered and demonstrated surprisingly novel biological roles for IL-22 in maintenance and regeneration of thymic function and bone marrow derived white blood cell development into subsets.

I. IL-22 Mediated Endogenous Regeneration of the Thymus.

During the development of the present inventions, the inventors found that a lack of IL-22 during development demonstrated that either there was a limited role for IL-22 or compensatory mechanisms were present for normal thymopoiesis. Thus it was a surprise that pronounced effects were observed following immune-depletion of IL-22–/– animals by irradiation. It was even more surprising that following radiation damage there was profound impairment of thymopoiesis when a subject was deficient for IL-22, such as shown in a mouse IL-22 KO. This impairment was pronounced when severe thymic depletion of both stromal and hematopoietic compartments was observed.

This newly discovered role for IL-22 in effecting thymic regeneration was further highlighted by measuring a significant increase in intrathymic production of IL-22 during periods of regeneration, on both an absolute and per cell basis, with or without hematopoietic stem cell transplant (HSCT). There is evidence to suggest that the primary producer of IL-22 in the thymus is an LTi-like (lymphoid-tissue inducer) or innate lymphoid cell expressing RORγ(t) and IL-7Ra. Both freshly isolated thymic epithelial cell (TEC) population and the TE-71 TEC line expressed the IL-22Rcc demonstrating a cellular target in vivo for IL-22 induced responses.

Further, following a screen of thymic cell types in order to identify the cellular source of IL-22 in the thymus, a population found consistently with gene expression for IL-22 was mTECs. However on closer examination at the protein level, while confirming the PCR data that IL-22 was expressed by mTECs, there were very low levels detected at the limits of the assay. This result indicated that a similarly sized cell population identified by expression of tissue-restricted antigens for tolerance induction might be the IL-22 producing cell type. In fact this hypothesis was further supported by the fact that the majority of IL-22 producing mTECs were MHCII$^{hi}$, which is also indicative of Aire expression and subsequently expression of TRAs. Therefore, during the development of the present inventions these cell types were tested for IL-22 mRNA, see below.

Further indicating its mechanism, in vitro incubation of TE-71 cells with IL-22 led to significantly increased phosphorylation of STAT-1, 3 and 5 which are capable of mediating IL-22R signalling in addition to aiding in survival of freshly isolated TECs in vitro. To assess if IL-22 itself could aid in thymic regeneration recombinant mouse IL-22 was administered to irradiated mice and found to significantly enhance thymic cellularity comprised of increased thymocytes and stromal cells, including TECs, fibroblasts and endothelial cells.

Despite the presence of IL-22 detected in mTECs, by far the most potent cellular producer of IL-22 in the thymus was discovered to be LTi-like cells. LTi-like cells are also present in the gut and expressed the markers associated with LTi cells, such as IL-7Rα, RORγ(t), CCR6 and lacking NKp46.

Taken together these findings demonstrated a distinct mechanism of endogenous thymic regeneration and outline a novel biological role for IL-22 in post-natal thymic function. Moreover these findings lay a solid foundation for the use of IL-22 as a therapeutic strategy for immune regeneration for clinical use as a therapeutic treatment of subjects.

Hematopoietic stem cell transplant (HSCT) is one of a small number of curative therapies for leukemia patients and others with hematological malignancies. Its use, however, is restricted by several major complications, including induction of graft versus host disease (GvHD), malignant relapse and post-transplant immune deficiency. In contrast to the relatively early recovery of platelets, erythrocytes, and leukocytes involved in innate immunity, recipients (in particular adults) of a HSCT experience prolonged post-transplant deficiency in the recovery of adaptive immunity. This period of prolonged immune deficiency, which is especially devastating to the T cell compartment, leads to a significant delay in the recovery of function and T cell repertoire (1-3) and subsequently to an increase in opportunistic infections and higher treatment-associated morbidity and mortality (4) In fact, the risk of opportunistic infection in the post-transplant period is directly correlated to the recovery of T cells, and in particular CD4+ T cells (1, 2, 5 and 6) The severity and duration of this immune deficiency is influenced by several factors such as previous chemo- or radiation-therapy, GvHD and donor/host incompatibility, however, there is a clear inverse relationship between transplant recipient age and the capacity to generate new T lymphocytes. Optimal T cell development requires a functional thymus and many patients who could benefit from enhancing immune regeneration have poor thymic function due to their age or their exposure to chemo- and radiation therapy.

Hence one of the most significant clinical challenges is the need for rapid regeneration of thymopoiesis following induced immunodepletion and transplantation. Thymopoiesis is a highly complex process involving the cross-talk between developing thymocytes and the non-hematopoietic supporting stromal microenvironment (7), which is comprised of highly specialized epithelial cells, endothelium, fibroblasts and dendritic cells. Thymic epithelial cells (TECs) can be separated into two populations that differ both in their spatial location and function within the thymus. Cortical (cTECs) are predominantly involved with the differentiation of T cell progenitors that, in addition to fibroblasts, act as potent producers of critical T cell development cytokines and growth factors such as IL-7, SCF, CXCL12, CCL17, CCL21, CCL25, etc. In contrast mTECs, in combination with thymic dendritic cells (tDCs), were critical for the induction of negative selection through their production of tissue restricted antigens (TRAs) under the control of regulators such as Aire. Expression of Aire, and subsequent production of TRAs, is associated with upregulation of MHCII and CD80 and marks the transition to mature mTECs that are thought to have undergone terminal differentiation.

IL-22 is an IL-10 family cytokine that was predominantly associated with maintenance of barrier function at mucosal surfaces (8). IL-22 signaling was shown to play a critical role in host defense, especially at barrier surfaces (8) and leads to the expression of innate defense molecules such as S100 proteins, defensins and Reg molecules (9-12). The IL-22R is a heterodimer formed from the IL-10Rβ and a specific IL-22Rα and is restricted to non-hematopoietic cells, thus far identified in skin, pancreas, intestine, liver, lung and kidney (9, 13). The primary source of IL-22 has remained controversial and largely depends on the model being used, however several innate lymphoid cells were identified as potent in vivo sources of IL-22 including LTIs, TH17 cells, NKp46+ cells (including NK cells) and DCs (14-24).

The bone marrow is a non-epithelial organ and therefore, the inventors were further surprised to discover that IL-22 also had an apparent role in lymphoid vs. myeloid lymphocyte lineage commitment in the bone marrow.

As described herein, the role of IL-22 was discovered in the regeneration of the thymus following insult such as radiation therapy. IL-22 was found herein to be produced in the thymus in response to injury and further to have mediated the endogenous regeneration of the thymus. Importantly IL-22 is contemplated for use by the inventors as a therapeutic agent to significantly enhance thymic function following radiation damage. These primary effects of IL-22 were seen predominantly within thymic epithelial cells and endothelium, effects such as function and viability. These findings present IL-22 as a cytokine regulating novel thymic function, particularly in regenerative periods following injury. Moreover, a novel approach is provided for restoring immune capacity to overcome lymphocytopenia or to stimulate lymphocyte regeneration, including situations of HSCT, high dose chemotherapy, AIDS, vaccination, tolerance-induction or directed tumor therapies in subjects.

The following references are herein incorporated by reference in their entirety.

1. Small, et al., Comparison of immune reconstitution after unrelated and related T-cell-depleted bone marrow transplantation: effect of patient age and donor leukocyte infusions. Blood 93:467-480 (1999).
2. Storek, et al., Immunity of patients surviving 20 to 30 years after allogeneic or syngeneic bone marrow transplantation. Blood 98:3505-3512 (2001).
3. Storek, et al., T cell reconstitution after bone marrow transplantation into adult patients does not resemble T cell development in early life. Bone Marrow Transplant 16:413-425 (1995).
4. van den Brink, et al., Strategies to enhance T-cell reconstitution in immunocompromised patients. Nat Rev Immunol 4:856-867 (2004).
5. Maury, et al., Prolonged immune deficiency following allogeneic stem cell transplantation: risk factors and complications in adult patients. Br J Haematol 115:630-641 (2001).
6. Storek, et al., Infectious morbidity in long-term survivors of allogeneic marrow transplantation is associated with low CD4 T cell counts. Am J Hematol 54: 131-138 (1997).
7. Petrie, et al., Zoned out: functional mapping of stromal signaling microenvironments in the thymus. Annu Rev Immunol 25:649-679 (2007).
8. Sonnenberg, et al., Border patrol: regulation of immunity, inflammation and tissue homeostasis at barrier surfaces by IL-22. Nat Immunol 12:383-390 (2011).
9. Wolk, et al., IL-22 Increases the Innate Immunity of Tissues. Immunity 21:241-254 (2004).
10. Liang, et al., Interleukin (IL)-22 and IL-17 are coexpressed by Th17 cells and cooperatively enhance expression of antimicrobial peptides. The Journal of Experimental Medicine 203:2271-2279 (2006).
11. Boniface, et al., IL-22 inhibits epidermal differentiation and induces proinflammatory gene expression and migration of human keratinocytes. J. Immunol. 174:3695-3702 (2005).
12. Wolk, et al., IL-22 regulates the expression of genes responsible for antimicrobial defense, cellular differentiation, and mobility in keratinocytes: a potential role in psoriasis. Eur J Immunol 36:1309-1323 (2006).
13. Tachiiri, et al., Genomic structure and inducible expression of the IL-22 receptor alpha chain in mice. Genes Immun. 4:153-159 (2003).
14. Zheng, et al., Interleukin-22 mediates early host defense against attaching and effacing bacterial pathogens. Nat Med 14:282-289 (2008).
15. Guo, et al., Interleukin-22 (IL-22) production by pulmonary Natural Killer cells and the potential role of IL-22 during primary influenza virus infection. J Virol 84:7750-7759 (2010).
16. Zenewicz, et al., Innate and adaptive interleukin-22 protects mice from inflammatory bowel disease. Immunity 29:947-957 (2008).
17. Wolk, et al., Cutting edge: immune cells as sources and targets of the IL-10 family members? J. Immunol. 168: 5397-5402 (2002).
18. Awasthi, et al., Cutting edge: IL-23 receptor gfp reporter mice reveal distinct populations of IL-17-producing cells. J. Immunol. 182:5904-5908 (2009).
19. Spits, et al., The expanding family of innate lymphoid cells: regulators and effectors of immunity and tissue remodeling. Nat Immunol 12:21-27 (2011).
20. Sawa, et al., ROR[gamma]t+ innate lymphoid cells regulate intestinal homeostasis by integrating negative signals from the symbiotic microbiota. Nat Immunol 12:320-326 (2011).
21. Cella, et al., A human natural killer cell subset provides an innate source of IL-22 for mucosal immunity. Nature 457: 722-725 (2009).
22. Takatori, et al., Lymphoid tissue inducer-like cells are an innate source of IL-17 and IL-22. J Exp Med 206:35-41 (2009).
23. Cella, et al., Expansion of human NK-22 cells with IL-7, IL-2, and IL-1beta reveals intrinsic functional plasticity. Proc Natl. Acad Sci USA 107:10961-10966 (2010).
24. Hughes, et al., Interleukin-1beta selectively expands and sustains interleukin-22+ immature human natural killer cells in secondary lymphoid tissue. Immunity 32:803-814 (2010).
25. Gray, et al., Unbiased analysis, enrichment and purification of thymic stromal cells. J Immunol Methods 329:56-66 (2008) and Wolk, et al., Biology of interleukin-22, Semin Immunopathol (2010) 32:17-31; U.S. Pat. No. 7,226,591; United States Patent Appln. No. US2003/0100076; Manley and Condie, Progress in Molecular Biology and Translational Science, 92:103-120 (2010); Heng et al., Current Opinion in Pharmacology 2010, 10:425-433; and Manley et al., Seminars in Immunology, Vol. 12, pp. 421-428 (2000).

II. Interleukin-22 Induced Endogenous Thymic Regeneration In Mice.

Thymopoiesis is a complex process involving cross-talk between developing thymocytes and the non-hematopoietic supporting stromal microenvironment, which is comprised of specialized thymic epithelial cells (TECs), endothelium, fibroblasts and dendritic cells (DCs). TECs can be separated into two populations, cortical TECs (cTECs) and medullary TECs (mTECs), which differ in their spatial location and function within the thymus. IL-22 is primarily associated with the maintenance of barrier function and induction of innate antimicrobial molecules at mucosal surfaces (Aujla, et al., IL-22: a critical mediator in mucosal host defense. J Mol Med 87:451 (2009); Sonnenberg, et al., Border patrol: regulation of immunity, inflammation and tissue homeostasis at barrier surfaces by IL-22. Nat Immunol 12:383 (2011), each of which is herein incorporated by reference in their entirety). The principal sources of IL-22 are T helper 17 cells (TH17) and innate lymphoid cell (ILC) subsets (Spits, et al., The expanding family of innate lymphoid cells: regulators and effectors of immunity and tissue remodeling. Nat Immunol 12:21 (2011); Sawa, et al., RORg(t)+ innate lymphoid cells regulate intestinal homeostasis by integrating negative signals from the symbiotic microbiota. Nat Immunol 12:320 (2011); Cella, et al., A human natural killer cell subset provides an innate source of IL-22 for mucosal immunity. Nature 457:722 (2009); Takatori, et al., Lymphoid tissue inducer-like cells are an innate source of IL-17 and IL-22. J Exp Med 206:35 (2009), each of which is herein incorporated by reference in their entirety).

Endogenous thymic regeneration is an important function that allows for renewal of immune competence after stress, infection or immunodepletion. As described herein, a framework of thymic regeneration centered on IL-22 as triggered by depletion of CD4+CD8+ double positive (DP) thymocytes. Intrathymic levels of IL-22 were discovered to increase following thymic insult while thymic recovery was impaired in IL-22-deficient mice. IL-22, which signalled through thymic epithelial cells (TECs) and promoted their proliferation and survival, was upregulated by radio-resistant RORγ(t)+CCR6+NKp46− lymphoid tissue-inducer cells (LTi) after thymic injury in an IL-23 dependent manner.

Administration of IL-22 was discovered during the development of the present inventions to enhance thymic recovery following total body irradiation (TBI). Thus, in one embodiment, methods are provided for treating immunocompromised patients with IL-22. In one embodiment, methods are provided for treating immunocompromised patients with cells secreting IL-22. In preferred embodiments, treatments of immunocompromised patients results in improved recovery of thymocyte production and improved function of mature thymocytes. As described herein, these studies revealed mechanisms of endogenous thymic repair which are contemplated for use to design innovative regenerative strategies for improving immune competence in patients.

Despite being exquisitely sensitive to insult, the thymus is remarkably resilient in young healthy animals. However, thymic renewal after immune depletion is a prolonged process, particularly in elderly patients, which substantially impairs the recovery of adaptive immunity. This period of prolonged immune deficiency leads to an increase in opportunistic infections and higher treatment-associated morbidity and mortality. Thus, in another embodiment, elderly patients with reduced immune function are treated with IL-22. In another embodiment, elderly patients with reduced immune function are treated with cells secreting IL-22. The age-related impaired immune system is a major problem when rapid immune recovery is required such as following induced immune depletion (chemotherapy, TBI for HSCT) or even in the recovery from infection or stress. Thus, manipulating the IL-22 regenerative pathway is contemplated to contribute to the recovery in aged individuals in these instances. In summary, IL-22 enhanced TEC proliferation and survival, and thus enhanced thymopoiesis.

III. Additional Demonstrations that IL-22 Enhanced Bone Marrow Hematopoiesis.

During the development of the present inventions, the inventors discovered IL-22 effects on hematopoiesis, in particular of altering white blood cell development in the bone marrow.

Exemplary data shown herein and obtained during the development of the present inventions indicated that IL-22 impacted BM hematopoiesis, see also FIG. 9 in addition to FIG. 25. In particular, in mice deficient for IL-22, IL-22-KO, but otherwise untreated, there was reduced lymphopoiesis and increased myelopoiesis (FIG. 25A). IL-22 also regulated hematopoietic stem cell (HSC) numbers as, by phenotype, Lin− Sca1+ckit+CD150+CD48−, were reduced in IL-22−/− mice (FIG. 25A). In mice deficient for IL-22 that had been challenged with TBI, they showed reduced lymphopoiesis (FIG. 25B).

IL-22 targeted Nestin+ cells in the bone marrow (BM) (FIG. 25C). This population was recently found to be a major support cell of hematopoiesis in the BM. Data also indicated that fatality due to poor engraftment in recipients of HSCT is far greater in mice deficient for IL-22 (FIG. 25D). Taken together, these findings indicated that methods comprising IL-22 are contemplated for: 1) promoting engraftment of HSCs, 2) promoting differentiation and thus reconstitution ability of HSCs, and 3) promoting BM hematopoiesis after immune stressors such as radiation injury, etc.

Thus in one embodiment, when a subject has a condition of altered bone marrow immune cell generation, such that bone marrow derived stem cells have decreased lymphoid cells; administering said therapeutic IL-22 composition to said subject is contemplated for enhancing production of bone marrow derived lymphoid cells. In a further embodiment, said lymphoid cells are a population of cells containing an increased number of mature functional lymphoid cells. In another embodiment, methods comprising IL-22 and cells secreting IL-22 are contemplated to promote engraftment of hematopoietic stem cells. In another embodiment, methods comprising IL-22 and cells secreting IL-22 are contemplated for differentiation of hematopoietic stem cells for increasing the reconstitution ability of these stem cells. In another embodiment, methods comprising IL-22 and cells secreting IL-22 are contemplated for improving bone marrow (BM) hematopoiesis after immune stressors such as radiation injury.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); µm (micrometers); nm (nanometers); .degree. C. (degrees Centigrade); Gy (gray) and cGy (centigray).

Example 1

Materials and Methods.

This Example describes exemplary materials and methods used herein. For animal studies, inbred C57Bl16, Ly5.1, BALB/c and B10.Br mice were obtained from the Jackson Laboratories (Bar Harbor, Me., United States of America (USA)). IL-22$^{-/-}$ animals were provided by Genentech (South San Francisco, Calif.). Mice were maintained at the Research Animal Resource Center, Memorial Sloan-Kettering Cancer Center (New York, USA). Animals were allowed to acclimatize for at least 2 days before experimentation, which was performed according to Monash University animal experiment ethics committee guidelines and which approved these studies.

The following table shows exemplary levels of irradiation with number and type of donor cells used for certain treatments, see below.

Models of Immune Degeneration

| Treatments | Abbreviations and details | Irradiation | Cell number, Donor Genotype and Tissue |
|---|---|---|---|
| Sublethal total body irradiation (Sublethal TBI) | Sublethal TBI | 1 × 550 cGy | None |
| Syngeneic BMT (bone marrow transplant) cells | syn-BMT | 2 × 550 cGy | 5 × 10$^6$ Ly5.1 BM |
| Allogeneic BMT | allo-BMT B6 recipient | 2 × 550 cGy | 5 × 10$^6$ B10 · Br BM |
| Allogeneic BMT | allo-BMT BALB/c recipient | 2 × 425 cGy | 5 × 10$^6$ B6 BM |

Cell Isolation

Individual or pooled single cell suspensions of freshly dissected thymuses were obtained from digested thymus tissue as previously described[25].

Flow Cytometry Reagents

The following fluorochrome labeled antibodies against Murine antigens (as well as appropriate isotype controls) were used: Alexa Fluor 700-conjugated anti-CD34 (RAM34), PE or biotin-conjugated anti-Ly51 (6C3), PE-conjugated anti-IL-22Rα, PE-Cy7-conjugated anti-CD31, PE-Cy7 or PE-conjugated anti-CD 11c, PE-Cy7 or Pacific Blue-conjugated anti-CD8, APC-conjugated anti-CD117 (2B8), PercP-eFluor 710 or PE-conjugated anti-IL-22, PercP-eFluor 710-conjugated anti-RORγ(t), Fitc-conjugated anti-CD19, CD11b, Ly6G, PercP-eFluor 710, APC or Biotin-conjugated anti-EpCAM (G8.8), APC-conjugated anti-CD140a, Biotin-conjugated anti-CD140b, APC-eFluor 780-conjugated anti-CD45, Fitc or APC-eFluor 780-conjugated anti-TER119 (TER119), APC-eFluor 780-conjugated anti-TCRβ, PE-Texas Red-conjugated anti-CD25, Alexa Fluor 700-conjugated anti-CD90.2, Qdot 655-conjugated anti-B220, eFluor 450-conjugated anti-CD44 (IM7), Pacific Blue-conjugated Qdot 605-conjugated anti-CD4 (2B11/CXCR4), Biotin-conjugated anti-H-2 Kb, Fitc, eFluor450, PE-Cy7 or biotin-conjugated anti-CD45.1 (A20), FITC or biotin-conjugated anti-CD45.2. Secondary reagents used were Qdot 525, Qdot 655 or Qdot 705-conjugated to streptavidin. All conjugates were purchased from eBiosciences, Biolegend, BD Biosciences, Molecular Probes or R&D Systems. Flow cytometric analysis was performed on an LSRII (BD Biosciences) and cells were sorted on an Aria II (BD Biosciences) using FACSDiva (BD Biosciences) or FlowJo software (Treestar Software, Ashland, Oreg., USA).

PhosFlow

For PhosFlow staining of STATS, TE-71 cells were allowed to settle for approximately 6 hours and then incubated+/−IL-22 (100 ng/mL) for 1 hour. Cells were then harvested and phospho-STAT expression was measured.

Enzyme-linked Immunosorbent Assay (ELISA)

Thymuses were suspended in 2 mL FACS Buffer (PBS with 0.5% BSA+2 mM EDTA), centrifuged and supernatant collected for ELISA. IL-22, IL-23 and IL-25 ELISA kits purchased from Biolegend (San Diego, Calif.) and performed as per the manufacturers instructions.

Intracellular STAT Signaling

For all assays requiring analysis of intracellular antigens, cells were fixed and permeablized as previously described. Briefly, cells were fixed in 1.6% paraformaldehyde for 10 minutes at 37° C. followed by 90% methanol for 10 minutes at 4° C. After thorough washing to completely remove methanol, cells were stained for both intracellular and extracellular antigens. For intracellular IL-22 staining, cells were incubated for 3 hours with Brefeldin (ng/mL) with or without IL-23 (ng/mL). MHCII$^+$ cells were enriched using magnetic bead separation on an AutoMACS (Miltenyi Biotech, Cambridge, Mass., USA).

Example 2

IL-22 Is Redundant or not Required for Steady-State Thymopoiesis During Development.

This example shows an exemplary demonstration of changes in lymphocyte populations resulting from a lack of IL-22 during development.

To assess the impact of IL-22 on thymopoiesis 8 week-old C57Bl/6 mice deficient for IL-22 were analyzed. Thymuses from WT and IL-22$^{-/-}$ animals were analyzed by flow cytometry and compared, by composition of subsets, within both hematopoietic and stromal compartments after digestion of tissue into a single cell population.

There was no difference in thymic cellularity of IL-22$^{-/-}$ animals, reflected by no change in developing CD4$^-$CD8$^-$ and CD8$^+$CD4$^+$ thymocytes (FIG. 1A). However, while there was no change in the number of CD4$^+$ single positive (SP) thymocytes, a significant decrease in the number of CD8$^+$ cells was observed (FIG. 1A). Reflecting this change in SP thymocytes within the stromal compartment no change was observed in the number of CD45$^-$EpCAM$^+$MHCH$^+$Ly51$^+$ UEA1$^{lo}$ cortical TECs (cTEC) but a significant reduction in CD45$^-$EpCAM$^+$MHCII$^+$Ly51$^{lo}$UEA1$^{hi}$ medullary TECs (mTEC) as well as CD45$^-$ EpCAM$^-$CD31$^+$ endothelial cells was observed (FIG. 1D). FIG. 1:A). Exemplary total thymic cellularity and the total number of CD4$^+$CD8$^+$ DP (double positive), CD4$^+$ SP (single positive) TCRβ$^+$ or CD8$^+$ SP TCRβ$^+$ thymocytes. Concatenated flow cytometric plots of CD4 vs CD8 in samples displayed. B). Exemplary concatenated flow cytometry plot detailing ratio of cTEC to mTEC. Gated on DAPTCD45$^-$EpCAM$^+$MHCII$^+$ cells. C). Exemplary frequency of cTEC and mTEC within the thymus of WT and IL-22$^{-/-}$ animals. D). Exemplary total number of cTEC, mTEC, Fibroblasts and endothelial cells in the thymus. FIG. 8: Exemplary demonstration of thymic size and IL-22 production. a) Total thymic cellularity at day 7 in animals treated with doses of radiation from 100-500 cGy. b) IL-22 expression in thymocytes and thymic stromal cells (gray curves).

Example 3

IL-22 Induced Thymic Regeneration Following Immunodepletion.

This example shows an exemplary demonstration of significant impairment of thymic regeneration in mice deficient for IL-22 and an IL-22 requirement for thymic regeneration following immunodepletion. FIG. 2-1: A). Total number of cells in the thymus of WT B6 or IL-22$^{-/-}$ B6 animals 7, 14 or 28 days after sublethal (1×550 cGy) irradiation. B). Total number of CD4$^+$CD8$^+$, TCRβ$^+$CD4$^+$ or TCRβ$^+$CD8$^+$ thymocyte subsets at day 28 in three models of immune depletion. The models examined were: TBI-alone (1×550 cGy in WT or IL-22$^{-/-}$ B6 animals); syngeneic-BMT (2×550 cGy+ 5×10$^6$ Ly5.1 BM donor cells transplanted into WT or IL-22$^{-/-}$ B6 recipients); or allogeneic-BMT (2×550 cGy+5×10$^6$ TCD B6 BM donor cells transplanted into WT or IL-22$^{-/-}$ BALB/c recipients). C). Total number of thymic stromal cells (Fibroblasts, Endothelium, mTECs and cTECs) in the aforementioned models of immune depletion at 28 days after treatment. Exemplary results are shown in Table 1.

Example 4

Intrathymic IL-22 was Significantly Increased in Periods of Regeneration.

Exemplary demonstration of IL-22 produced as a response to thymic damage shown as intrathymic IL-22 was significantly increased in periods of thymic regeneration.

To assess the levels of IL-22 within the thymus in these models of thymic regeneration, single-cell suspensions of thymus were generated and supernatant collected for ELISA.

IL-22 was measured by ELISA in animals that were untreated or 7 days after irradiation alone (550 cGy), syngeneic-BMT (2×550 cGy+5×10$^6$ Ly5.1 BMC) or allogeneic-BMT (2×550 cGy+5×10$^6$ TCD B6 BMC).

A significant increase in the absolute quantity of IL-22 within the thymus 7 days following irradiation, with or without syngeneic or allogeneic HSCT (FIG. 3A) was found. This finding was particularly surprising due to the significant decrease in the total cellularity of the thymus in these models.

Example 5

Intrathymic IL-22 Production was Upregulated Following Thymic Insult and Correlated Inversely with Thymic Damage.

To measure if levels of IL-22 in the thymus change in conditions of immune regeneration, ELISA was used to measure IL-22 protein Animals were examined seven days after given sublethal irradiation (550 cGy) or lethal irradiation (2×550 cGy)+ syngeneic-BMT (bone marrow transfer) (5×10$^6$ Ly5.1 BM (bone marrow)) or allogeneic-BMT (5×10$^6$ BM cells from B10.Br or B6 donors into B6 (2×550 cGy) or BALB/c (2×425 cGy) respectively). In each of these models of immune depletion significantly increased levels of intrathymic IL-22 was present (FIG. 3A) at day 7. These findings in absolute levels of intrathymic IL-22 were particularly striking due to the significant decrease in the total cellularity of the thymus in these models. Together these findings demonstrated a strong inverse correlation (p<0.0001, r$^2$=0.6669) between thymic size and absolute amount of intrathymic IL-22 present (FIG. 3E). To further explore this correlation between thymic size and levels of IL-22, doses of radiation were titrated to give degrees of thymic damage. In this model intrathymic levels of IL-22 were significantly increased, even at the lowest levels of radiation damage indicating that even mild damage triggers the production of IL-22. Surprisingly, while the radiation titration did indeed lead to more severe thymic insult, as measured by total thymic cellularity, the levels of IL-22 did not significantly increase over and above those observed in the lowest radiation group.

A significant increase in the absolute quantity of IL-22 within the thymus 7 days following irradiation, with or without syngeneic or allogeneic HSCT was measured (FIG. 3A). This finding was particularly significant due to the significant decrease in the total cellularity of the thymus in these models.

Example 6

Exemplary Demonstration of Administration of Recombinant IL-22 which Caused Significantly Enhanced Thymic Regeneration Following Insult/Damage. IL-22 is Produced in an Autocrine Fashion by TECs.

To identify the intrathymic source of IL-22, thymuses were digested and fixed immediately to look for intracellular IL-22 by FACS. No IL-22 was detected within hematopoietic populations of developing thymocytes as well as within the endothelial and fibroblast stromal populations. In contrast, a small but consistent shift in population peaks was observed on flow plots which indicated IL-22 expression in both cTEC and mTEC populations (FIG. 3G) This finding at the protein level was confirmed at the mRNA expression level by qPCR (quantitative PCR). Subsets of thymocytes and stromal cells were sorted and IL-22 expression measured by qPCR. An IL-22 signal was not observed in developing double positive (DP) or single positive (SP) thymocytes nor within fibroblasts or endothelium. Surprisingly, significant expression of IL-22 in both cTEC and mTEC populations was observed, a potential indication of autocrine production.

To confirm this IL-22 production, supernatant from TE-71 cell cultures were analyzed for presence of IL-22 by ELISA. Of the 10 cultures tested for presence of IL-22 low but detectable levels were measured in 5 of those cultures. Due to the very low levels of IL-22, near the limit of detection for the assay, it is likely that the wells that tested negative did indeed have IL-22 but were below the threshold of detection for this particular assay. The low IL-22 amounts that were measured indicated that IL-22 was being produced by TECs and in very low quantities in TE-71 cells and may be indicative of TRA expression rather than as an active cytokine.

To confirm this expression by TECs, a MHC-II positive cell population was enriched from thymic tissue using magnetic bead separation (Miltenyi Biotech autoMACS using anti-MHCII beads). The resulting fraction was incubated in the presence or absence of IL-23 for inducing IL-22 production for 3 hours followed by intracellular cytokine staining performed to measure the amount of IL-22 on a per-cell basis. However, a low amount of intracellular IL-22 was detected with this assay in TECs. In other murine studies one of the most potent producers of IL-22 were RORγ(t)$^+$ (Retinoid-Related Orphan Receptorγt) lymphoid-tissue inducer cells in mucosal tissue. In order to determine whether these cells add to thymic production of IL-22, total thymic cells were cultured in the presence or absence of IL-23 and stained for intracellular IL-22 in association with LTi markers. Surprisingly, significant staining was observed within the CD3$^-$CD8$^-$CD45$^+$IL7Rα$^+$RORγ(t)$^+$ cells. Due to the difficulty of staining for RORγ(t) in the thymus, which has very high endogenous expression of RORγ(t) in developing thymocytes, in addition to RORγ(t) other LTi markers were used including CD45, CD4, CD3, IL7Rα and RANKL. FIG. 3: a). Absolute level of IL-22 in the thymus in 3 models of immune depletion. The models used were untreated, 7 days after irradiation alone (550 cGy), syngeneic-BMT ($2\times550$ cGy+$5\times10^6$ Ly5.1 BMC) or allogeneic-BMT ($2\times550$ cGy+$5\times10^6$ TCD B6 BMC). b). Correlation between total thymic size and absolute levels of intrathymic IL-22. Data includes the aforementioned models of immune depletion. In addition: the therapeutic strategies of thymic regeneration keratinocyte growth factor (KGF) or leutenizing hormone releasing hormone analogue (LHRH-A) alone or in combination following allogeneic-HSCT ($2\times425$ cGy+$5\times10^6$ T cell depleted BM from B6 donors into BALB/c recipients); 56 days after TBI-alone or allogeneic-BMT (B10.Br into B6 recipients). c). Absolute levels of intrathymic IL-22 in different levels of thymic damage. IL-22 was measured 7 days after B6 animals were treated with 100, 200, 300, 400 or 500 cGy radiation. d). Correlation of thymic size and intrathymic IL-22 7 days after B6 animals were treated with 100, 200, 300, 400 or 500 cGy radiation. e). Relative change compared to housekeeping gene (HPRT) in different subsets of thymocytes or thymic stromal cells. f). Levels of IL-22 in cell cultures of the TEC line TE-71 cells (3 days of culture). g). Flow cytometry of mTECs and cTECs staining for IL-22 expression. h). IL-22 protein expression in intrathymic CD3$^-$CD45$^+$IL7Rα$^+$RORγ(t)$^+$LTi-like cells.

Example 7

Administration of Recombinant IL-22 Led to Enhanced Thymopoiesis.

To examine the clinical effectiveness of IL-22 as a regenerative strategy B6 animals were treated with PBS or recombinant mouse IL-22 (Genescript, Piscataway, N.J., USA). Treatment was administered to mice (4 μg/mouse/day for three days) at days-1, 0 and +1 of following irradiation and transplant. Total thymic cellularity at days 7 and 28 after irradiation. Models used were TBI-alone ($1\times550$ cGy) or syngeneic-BMT ($2\times550$ cGy+$5\times10^6$ Ly5.1 BM cells).

A significant increase in thymic cellularity was observed at both day 7 and day 28 compared to PBS treated controls in mice receiving sublethal irradiation alone (FIG. 4). Surprisingly, in animals that received lethal TBI in combination with syngeneic BMT a significant increase in thymus size was observed at day 7 but no change at day 28. This finding was consistent with IL-22 production correlation to thymic size. While in the syngeneic-BMT model there was considerable thymic regeneration within the PBS group, in animals receiving TBI alone there was still significant impairment of thymus cellularity at day 28.

Example 8

IL-22R was Expressed by TECs and Thymic Endothelium.

To assess the cellular targets of IL-22 in the thymus, cells were stained for presence of IL-22Rα by FACS. No detectable level of IL-22R was observed with this test on any thymocyte population or on thymic fibroblasts (FIG. 7).

While some staining was observed on thymic endothelium and dendritic cells, it was contemplated this staining was an artifact and represented cross-presentation in the case of DCs and stickiness in the case of endothelium. In both cTECs and mTECs, expression of IL-22Rα was easily detectable. Surprisingly, expression of IL-22Rα was considerably enriched within the more mature CD80$^+$ populations of TECs. Significant expression was observed on both cTECs and mTECs. Moreover, when TE-71 cells were stained for IL-22Ra a significant proportion of cells expressed the receptor.

Example 9

Exemplary Demonstration of IL-22 Signaling Through IL-22R which Induced STAT Signaling in TECS. IL-22 Led to Signaling in TECs Through STAT-3 and STAT-5.

To test if IL-22 could functionally signal through IL-22R expressed by TECs, the TE-71 cells were incubated in the presence of IL-22 or media alone. To account for the potential endogenous presence of IL-22 wells were included that were treated with α-IL-22 or a pan JAK inhibitor (JAK-I). Phosphorylation of STATs-1, 3 and 5 was measured by FACS.

Significantly increased amounts of STAT-1 (pY701), STAT-3 (pY705) and STAT-5 (pY701) phosphorylation was measured in cells treated with IL-22 compared to both media alone, JAK-I and α-IL-22. Surprisingly with IL-22 treatment the phosphorylation of S727 was significantly decreased. An important observation considering the current view is different such that activation of this site on STAT-3 was shown to inhibit S727 signal. FIG. 5: a). IL-22R in CD80$^+$ and CD80$^-$ TECs. b). Flow cytometry plots outlining STAT signaling through the TEC line TE-71 treated with anti-IL-22, a pan JAK inhibitor (JAK-I) or IL-22 (100 ng). c). mean fluorescence intensity of STAT signaling after treatment with anti-IL-22, a pan JAK inhibitor (JAK-I) or IL-22 (100 ng). FIG. 7: Exemplary demonstration of IL-22R expression in various thymocytes and thymic stromal cell subsets.

Example 10

IL-22 Promoted Survival of TECs and Thymic Endothelium.

TE-71 cells or CD45-depleted thymus were incubated+/-IL-22 (100 ng/mL) for 2 hours or 24 hours (CD45- cells only) and EpCAM expression measured as a test of cell viability. FIG. 6: Exemplary demonstration of EpCAM expression in CD45-depleted cells uncultured or cultured for 2 or 24 hrs in the presence of PBS or IL-22 (100 ng).

Example 11

IL-22 Regulated Lymphopoiesis and Myeloid Cell White Blood Cell Development in the Bone Marrow.

PBS and IL-22 (4 μg/mouse/day) treated animals were analyzed 7 days after sublethal TBI ($1\times550$ cGy) for developing B cells, lymphoid progenitors and myeloid cells.

Absolute levels of IL-22 were measured by ELISA in the BM of WT B6 mice 7 days after sublethal TBI alone ($1\times550$ cGy), syngeneic (genetically identical) BMT ($2\times550$ cGy TBI of B6 mice+$5\times10^6$ Ly5.1 BM cells) or allogeneic (genetically different) BMT ($2\times550$ cGy TBI of B6 mice+$5\times10^6$ T cell depleted B10.Br BM cells). *, $p<0.05$; **, $p<0.01$.

Phenotypes of mice used were as follows: LT-HSC (long-term hematopoietic stem cell) Lin$^-$Sca1$^+$ckit$^+$(LSK) CD150$^+$CD48$^-$; MPP1, LSK CD150$^+$CD48$^+$; MPP2, LSK CD150$^-$CD48$^+$; LMPP (lymphoid-primed multipotent progenitor), LSK Flt3$^{hi}$CD150$^-$ CD48$^+$; pro-B cells, B220$^+$CD43$^+$IgM$^-$; pre-B cells, B220$^+$CD19$^+$CD43$^-$IgM$^-$; imm-B cells, B220$^+$CD19$^+$CD43$^-$IgM$^+$. FIG. 9: A: WT or IL-22$^{-/-}$ B6 mice were analyzed for numbers of developing B cells, myeloid cells and hematopoietic stem and progenitor cells. B: PBS or IL-22 (4 μg/mouse/day) treated animals were analyzed for developing B cells, lymphoid progenitors and myeloid cells. C: Absolute levels of IL-22 were measured by ELISA in the BM of WT B6 mice 7 days after sublethal TBI alone (1×550 cGy), syngeneic (genetically identical) BMT (2×550 cGy TBI of B6 mice+5×10$^6$ Ly5.1 BM cells) or allogeneic (genetically different) BMT (2×550 cGy TBI of B6 mice+5×10$^6$ T cell depleted B10.Br BM cells). *, p<0.05; **, p<0.01.

Example 12

This Example Shows an Exemplary Demonstration of the Importance of IL-22 for Endogenous Regeneration of the Thymus.

At baseline, untreated wildtype (WT) and mice genetically deficient in IL-22 (Il22$^{-/-}$) (Zheng, et al., Interleukin-22, a TH17 cytokine, mediates IL-23-induced dermal inflammation and acanthosis. Nature 445:648 (2007), herein incorporated by reference in its entirety) demonstrated no difference in total thymic cellularity or in numbers of the various thymic cell populations (FIG. 14A-D). Therefore, to explore the effects of IL-22 deficiency on thymic regeneration after insult, WT or Il22$^{-/-}$ mice were given sublethal total body irradiation (SL-TBI). Il22$^{-/-}$ mice demonstrated significantly impaired thymic regeneration for up to 28 days after SL-TBI (FIG. 10A) with significantly reduced numbers of developing thymocyte subsets, TECs and non-TECs (including endothelial cells and fibroblasts) (FIG. 10B-D).

Syngeneic hematopoietic stem cell transplantation (HSCT) and allogeneic HSCT was performed in order to determine IL-22 effects. In both cases significantly reduced thymic cellularity and reduced numbers of thymic cell subsets were observed in Il22$^{-/-}$ hosts (FIG. 15). Upon long-term follow-up, impaired thymic regeneration in Il22$^{-/-}$ mice was observed for up to 98 days after TBI (FIG. 10E). When Il22$^{-/-}$ mice were given a targeted dose of radiation to the thymus, these mice exhibited significantly reduced thymic regeneration compared to WT controls at day 7 (FIG. 10F), indicating that the systemic damage of TBI was not required for the impacts of IL-22 deficiency on thymic regeneration.

Example 13

In this Example, Thymic IL-22 Production was Measured in Mice Seven Days after SL-TBI without HSCT, Lethal TBI and Syngeneic HSCT or T Cell Depleted Allogeneic-HSCT.

In each of these models a 2-3-fold increase in absolute amounts of IL-22 compared to control mice that were not irradiated was observed (FIG. 10G). This was striking given the significant decrease in thymic cellularity seen in irradiated mice (FIG. 16A) leading to a profound increase in the amount of IL-22 on a per cell basis (FIG. 16B). Absolute amounts of IL-22 peaked on day 5, corresponding closely with the lowest point of thymic cellularity, and returned to normal amounts by day 10 as thymic cellularity returned to baseline (FIG. 10H). These findings revealed an inverse correlation (r=−0.8345) between thymic size and absolute amount of intrathymic IL-22 (FIG. 10I). The radiation dose was titrated to further explore the coupling between thymic cellularity and IL-22. Although increasing doses of radiation led to more severe thymic insult (FIG. 16C), peak absolute amounts of IL-22 were achieved at the lowest TBI dose (FIG. 16D), which suggests that only a partial loss of thymic cellularity is necessary for increased expression of IL-22. Importantly, mice given a range of radiation doses targeted directly to the thymus also significantly increased their intrathymic amounts of IL-22 (FIG. 16E). In these same mice there was no change in the amounts of IL-22 in the spleen after thymic irradiation suggesting that upregulation of intrathymic IL-22 is an intrinsic local response to thymic injury.

Example 14

After L-TBI a population of CD45$^+$IL-7Rα$^+$CD3$^-$CD8$^-$RORγ(t)$^+$ thymic ILCs (tILC) was Identified that Upregulated their Production of IL-22.

ILCs that express the transcription factor RORγ(t) were identified as potent producers of IL-22 (Cella, et al., A human natural killer cell subset provides an innate source of IL-22 for mucosal immunity. Nature 457:722 (2009); Sawa, et al., Lineage Relationship Analysis of RORg(t)+ Innate Lymphoid Cells. Science 330:665 (2010), each of which is herein incorporated by reference in their entirety). Moreover, CD4$^+$CD3$^-$ thymic LTi contributed towards TEC development and maturation (Rossi et al., RANK signals from CD4+3-inducer cells regulate development of Aire-expressing epithelial cells in the thymic medulla. J Exp Med 204:1267 (2007), herein incorporated by reference in its entirety). Three days after L-TBI (with no hematopoietic rescue) a population of CD45$^+$IL-7Rα$^+$CD3$^-$CD8$^-$RORγ(t)$^+$ thymic ILCs (tILC) was identified that upregulated their production of IL-22 (FIG. 11A). No detectable IL-22 expression was found by CD3+ or CD45− populations (FIG. 17A-C). Closer examination revealed that IL-22-producing tILCs in both untreated and TBI-treated mice uniformly expressed CD4 and CCR6 but not NKp46 (FIG. 11B), a phenotype consistent with that of LTi cells (Sawa et al., Lineage Relationship Analysis of RORγ(t)+ Innate Lymphoid Cells. *Science* 330:665 (2010), herein incorporated by reference in its entirety). Apart from its role in ILC function, RORγ(t) was advantageous for thymocyte development and was widely expressed in the thymus (Sun, et al., Requirement for RORgamma in thymocyte survival and lymphoid organ development. Science 288:2369 (2000), herein incorporated by reference in its entirety). Mice deficient for Rorc, the gene encoding for RORγ(t), contained normal amounts of intrathymic IL-22 (FIG. 11C) at baseline indicating that steady-state amounts of intrathymic IL-22 did not require RORγ(t) or LTi. However, in contrast to WT mice, Rorc$^{-/-}$ mice did not significantly increase their intrathymic amounts of IL-22 in response to TBI (FIG. 11C) suggesting that RORγ(t)+ LTi is aventagous for intrathymic upregulation in the production of IL-22 after thymic damage. Thymic LTi were present immediately after radiation (FIG. 11D), indicating they are radio-resistant for the period when the upregulation of IL-22 is important for thymic regeneration, and could persist for up to three months after L-TBI and HSCT (FIG. 17D). Furthermore, given the severe depletion of thymus cellularity early after TBI, their frequency increased significantly after L-TBI (FIG. 11E). After TBI, LTi also increased their expression of RANKL (FIGS. 2F and 17E).

Example 15

Regulation of IL-22 Production was Closely Associated with DC-Produced IL-23, and Ex Vivo Incubation of ILCs with IL-23 Stimulated Production of IL-22.

Three days after L-TBI increased expression by LTi of IL-23R and RORγ(t) was observed (FIGS. 11F and 17E), consistent with its importance in regulating IL-22. Intrathymic amounts of IL-23 were measured in vivo where increased IL-23 production after SL-TBI was observed, mirroring the kinetics of IL-22 (FIG. 11G). Mice genetically deficient in Il12b, the gene that encodes the p40 subunit of IL-12 and IL-23, showed no change in IL-22 production (FIG. 11H) and exhibited a defect in thymic regeneration after SL-TBI (FIG. 11I), which demonstrated that intrathymic TBI-induced production of IL-22 required p40. Consistent with this, IL-22 expression was increased by thymic LTi after IL-23 stimulation in vitro (FIG. 11J).

Example 16

Identifying a Source of Elevated Intrathymic IL-23 after TBI was then Determined.

Although some thymic DCs expressed IL-23 at baseline, a greater frequency expressed IL-23 after L-TBI (FIG. 11K). IL-23 expression was found in both CD103+ and CD103− thymic DCs in untreated mice; however, there was significant enrichment of IL-23+ thymic DCs expressing CD103 (FIG. 11L) in irradiated animals. This is consistent with the finding that mucosal CD103+ DCs are potent IL-23 producers (Siddiqui, et al., E-cadherin marks a subset of inflammatory dendritic cells that promote T cell-mediated colitis. Immunity 32:557 (2010), herein incorporated by reference in its entirety). To further explore the relationship between IL-22 and thymocyte cellularity (FIG. 10G), mutant animals with well-defined blocks in intrathymic T cell development (24) were examined for production of IL-22 and IL-23 (FIG. 12A). Mice blocked within the CD4-CD8− double negative (DN) stage of thymocyte differentiation, prior to developing CD4+ CD8+ double positive (DP) thymocytes, expressed significantly more intrathymic IL-22 and IL-23 than WT controls (FIG. 12B). In contrast, mice deficient for TCRa or CCR7, which lack mature CD4 or CD8 single positive (SP) thymocytes but have no loss of DP thymocytes (Petrie, et al., Zoned out: functional mapping of stromal signaling microenvironments in the thymus. Annu Rev Immunol 25:649 (2007), Mak, et al., Knockout mice: a paradigm shift in modern immunology. Nat Rev Immunol 1:11 (2001), each of which is herein incorporated by reference in their entirety), exhibited no upregulation of IL-22 and IL-23 (FIG. 12B). Stable intrathymic IL-22 and IL-23 were also observed in mice deficient for CD40 ligand (Cd40l$^{-/-}$) (FIG. 12B), which have a defect in mTECs, but normal numbers of DP and SP thymocytes (Gray, et al., Developmental kinetics, turnover, and stimulatory capacity of thymic epithelial cells. Blood 108:3777 (2006), herein incorporated by reference in its entirety). Consequently, there was a strong inverse correlation between the number of DP thymocytes and amounts of intrathymic IL-22 and IL-23 (FIG. 12C), further suggesting that depletion or absence of DP leads to upregulation of IL-22 and IL-23. This was confirmed by treatment with dexamethasone (Dex), which specifically depletes DP thymocytes (FIG. 11D), and led to upregulation of IL-22 and IL-23 in WT mice (FIG. 12D). Strikingly, increased IL-22 expression was detected in freshly isolated LTi from Dex-treated mice without incubation, in stark contrast to the low/un-detectable levels in untreated mice (FIG. 12E). Furthermore, in the TBI model, significantly increased expression of RORγ(t) in LTi isolated from Dex-treated mice compared to untreated controls was observed (FIG. 12F). Although IL-7 signaling was implicated in LTi maintenance (Kim, et al., OX40 ligand and CD30 ligand are expressed on adult but not neonatal CD4+CD3− inducer cells: evidence that IL-7 signals regulate CD30 ligand but not OX40 ligand expression J Immunol 174:6686 (2005), herein incorporated by reference in its entirety), similar numbers of LTi were found in Il7$^{-/-}$ and Rag1$^{-/-}$ mice, and there was an increase in Il7ra$^{-/-}$ mice (FIG. 17F), indicating the importance of LTi for the natural production of IL-22. This suggests that LTi themselves or even a extrinsic LTi stimulating factor, could be used as a regenerative therapy. Furthermore, both the frequency of LTi (FIG. 17G) and their baseline production of IL-22 (FIG. 17H) was increased compared to WT controls. In these models of thymic damage and mutant mouse strains there was a strong correlation (r=0.9554) between amounts of thymic IL-22 and IL-23 (FIG. 18).

Example 17

IL-22R is a Heterodimer of IL-10Rβ and IL-22Rα.

IL-22R expression was reported to be restricted to non-hematopoietic cells. No IL-22Rα was detectable on developing thymocytes or non-epithelial stromal cells (FIG. 19A). In contrast, IL-22Rα was expressed on cTECs as well as MHC class II high and low expressing mTECs (mTEC$^{hi}$ and mTEC$^{lo}$ respectively), a marker of TEC maturation (FIG. 13A). To test whether IL-22 could functionally signal through IL-22R expressed by TECs, the TE-71 TEC cell line was stimulated with IL-22. Consistent with mucosal epithelia (Pickert et al., STAT3 links IL-22 signaling in intestinal epithelial cells to mucosal wound healing. J Exp Med 206, 1465 (Jul. 6, 2009), herein incorporated by reference in its entirety), IL-22 stimulation of TE-71 cells led to activation-induced phosphorylation of STAT-3 and STAT-5 (FIG. 19B).

Example 18

To Assess the Impact of IL-22 on Primary TECs, CD45− Cells were Enriched and Incubated with IL-22 or Media Alone for 24 Hours.

Although there was significant attrition of EpCAM expression in untreated cells, those treated with IL-22 maintained greater EpCAM expression, representing viability, in culture (FIG. 13B-C). Indicative of this, the presence of IL-22 improved TEC survival and increased proliferation of cTECs and mTEC$^{lo}$ (FIG. 13D). There was no observed change in expression of apoptosis-related Annexin V or Bcl-2 proteins (FIG. 19C). These findings demonstrated that IL-22 signals through IL-22R on the surface of TECs, and in particular in cTECs and mTEC$^{lo}$. It is within this latter population that immature mTEC populations are currently believed to reside. Although it is possible that IL-22 acts as a maturation signal for mTECs, it is more likely that IL-22 primarily functions to induce proliferation and viability, given the uniform expression of IL-22R on immature mTEC$^{lo}$ and mature mTEC$^{hi}$, and given the preferential promotion of proliferation amongst mTEC$^{lo}$. To examine the clinical effectiveness of IL-22 as a regenerative strategy, recombinant IL-22 was administered to mice after SL-TBI. Significantly increased thymic cellularity at days 7 and 28 was observed, compared to controls, in mice receiving SL-TBI (FIG. 13E). Increases were also observed in developing thymocyte subsets (FIG. 13F) and TEC subsets (FIG. 13G). There was also a significant increase in the proliferation of cTECs and mTEC$^{lo}$ at early time points after IL-22 treatment (FIG. 13H). Importantly, IL-22-treated animals receiving L-TBI in combination with syngeneic HSCT showed significantly enhanced thymic recovery at day 7 (FIG. 20). In otherwise untreated animals given IL-22, no change was observed in total thymic cellularity, although there was a small increase in cTEC and mTEC$^{lo}$ proliferation (FIG. 21). These studies show that after thymic injury and specifically the depletion of DP thymocytes, upregulation of IL-23 by radio-resistant CD103+ thymic DCs induces IL-22 production by tILCs. This cascade of events leads to regeneration of the supporting epithelial microenvironment and, ultimately, to enhanced thymopoiesis (FIG. 22). In some embodiments, keratinocyte growth factor is contemplated for thymic regeneration although it appears to be redundant for thymic ontogeny (Gray, et al., Unbiased analysis, enrichment and purification of thymic stromal cells. J Immunol Methods 329:56 (2008), herein incorporated by reference in its entirety). In this instance, however, depletion of DP cellularity triggered a thymic molecular network to aid in its own regeneration. Interestingly, once the thymus has been restored, IL-22 production stabilized. Consistent with this, administration of IL-22 was a highly effective regenerative strategy after radiation damage, but had little effect in untreated mice or those with significant recovery after syngeneic HSCT.

Example 19

Exemplary Gene Expression is Shown after Treatment of Mice with IL-22.

The genes that were identified in this analysis fell broadly within two categories. In one category expressed genes were identified that directly promote the proliferation of cells including E2F2, Aif1, Dock8, Wnt2 and Ang4. In another category expressed genes were identified that regulate the response to extrinsic stimuli including Tnfrsf11b (which acts as a decoy receptor to RANKL), Criml (which regulates BMP signaling) and Socs3 (which can regulate IL-22R signaling). These findings suggested that IL-22 both directly promoted the proliferation of TECs in addition to regulating the functional response of TECs to other stimuli including (but not necessarily restricted to) RANKL and BMP signaling.

See, FIG. 23: A, Unbiased cluster analysis of gene expression that changed in PBS treated or IL-22 treated (200 mg/kg/day) mice given SL-TBI. B, Changed genes comparing IL-22 treated TECs, STAT-3 KO alveolar epithelium (GEO ID GDS3106) or activated STAT-3 in MEFs (GEO ID GSE2251).>1.3 fold change, $p<0.05$. C, Fold change of selected genes in CD45− cells isolated from mice given SL-TBI and treated with IL-22 or PBS. D, Relationship between genes identified as changed in TECs after treatment with IL-22. E, RANKL expression on LTi isolated from untreated or after TBI. F, TECs in WT, Il22−/−, or IL-22/KGF dKO mice. G-H, Total number of CD4+CD8+ double positive (DP) thymocytes (G) or TECs (H) in WT or IL-22/KGF dKO mice. Bar graphs represent mean±SEM.

Example 20

Exemplary Demonstration of the Depletion of Thymus Cellularity after TBI.

Prolonged thymic deficiency after cytoreductive conditioning is a significant clinical challenge. These studies showed the discovery of a mechanism involving IL-22 governing endogenous thymic regeneration in addition to providing a therapeutic strategy for immune regeneration in patients whose thymus has been irrevocably damaged. Due to the severe depletion of the thymus after damage, together with the large increase in absolute levels of IL-22 after thymic damage, led to a significant increase in the amount of IL-22 being produced on a per cell basis. FIG. 24: A, WT or IL-22 KO BALB/c mice were given L-TBI with T-cell depleted (TCD) B6 BM and B6 T cells to induce GVHD. Total thymus cells at 3 weeks after transplant. B, B6 mice were given L-TBI with TCD B10.BR BM with or without B10.BR T cells. Absolute levels of IL-22 were measured at day 7. C, ILC were enumerated by isolation from BALB/c mice 21 days after TBI with B6 BM alone or with the addition of B6 T cells to induce GVHD. D, ILCs isolated from BALB/c mice 21 days after TBI with B6 BM alone or with the addition of B6 T cells to induce GVHD were incubated in vitro with IL-23. Intracellular IL-22 expression was assessed in ILCs. E, B6 mice were given L-TBI with TCD LP BM alone (grey bars) or with LP T cells (black bars). Mice were also treated with PBS or rIL-22 (200 ug/kg/day) daily. Number of CD4+CD8+ thymocytes at 3 weeks after transplant.

Example 21

This Exemplary Example Provided Further Information on IL-22 Enhanced Bone Marrow Hematopoiesis.

Data obtained during the development of the present inventions indicated that IL-22 impacted BM hematopoiesis, see also FIG. 9 in addition to FIG. 25. In mice deficient for IL-22, IL-22-KO, but otherwise untreated, there was reduced lymphopoiesis and increased myelopoiesis, such as increased pre-B cells and immature B cell subsets (FIG. 25A). IL-22 also regulated hematopoietic stem cell (HSC) numbers as, by phenotype, Lin$^-$Sca1$^+$ckit$^+$CD150$^+$CD48$^-$, were reduced in IL-22−/− mice (FIG. 25A). In mice deficient for IL-22 that had been challenged with TBI, showed reduced lymphopoiesis (FIG. 25B). Exemplary data shown herein also indicated that IL-22 targeted Nestin+ cells in the BM (FIG. 25C). This population was discovered as a major support cell of hematopoiesis in the BM. Data indicated that fatality due to poor engraftment in recipients of HSCT was far greater in mice deficient for IL-22 (FIG. 25D). When IL-22 was used for treatment, see, 25E, certain subtypes were increased, including immature B cells, while macrophages and granulocyte numbers were decreased. Taken together, these findings indicated that methods comprising IL-22 are contemplated for: 1) promoting engraftment of HSCs, 2) promoting differentiation and thus reconstitution ability of HSCs, and 3) promoting BM hematopoiesis after immune stressors such as radiation injury, etc.

Example 22

The Following are Descriptions of Exemplary Materials and Methods Used for Examples 13-21.

Inbred mice included C57BL/6, Ly5.1, BALB/c, Il12b$^{-/-}$, Rag1$^{-/-}$, IL7$^{-/-}$, Tcra$^{-/-}$, Tcrb$^{-/-}$, Cd40l$^{-/-}$, and Ccr7$^{-/-}$ and were obtained from the Jackson Laboratories (Bar Harbor, USA). Il22$^{-/-}$ mice on BALB/c and C57Bl/6 backgrounds were provided by W. Ouyang (Genentech, San Francisco); Rorc$^{-/-}$ mice were provided by D. Littman (New York University, New York); and Il7ra$^{-/-}$ mice were provided by S. Prockop (Memorial Sloan-Kettering Cancer Center, New York). Mice were maintained at the Research Animal Resource Center, Memorial Sloan-Kettering Cancer Center (New York, USA). Animals were allowed to acclimatize for at least 2 days before experimentation. Experiments were performed according to Institutional Animal Care and Use Committee guidelines.

Models of thymic damage. Sublethal-TBI (SL-TBI), 1×550 cGy with no hematopoietic rescue; syngeneic-HSCT (syn-HSCT) 2×550 cGy+5×10$^6$ Ly5.1$^+$ BM cells; allogeneic-HSCT (C57Bl/6 MHC-mismatched recipient) 2×550 cGy+5×10$^6$ T cell depleted B10.Br BM cells; allogeneic-HSCT (BALB/c MHC-mismatched recipient) 2×425 cGy+5×10$^6$ T cell depleted Ly5.1$^+$ BM cells; 3 days following lethal-TBI (2×550 cGy) with no hematopoietic rescue (L-TBI). To recover sufficient cell numbers, each individual point within L-TBI groups represents 2-3 thymuses pooled together. TBI experiments were performed with a Cs-137 γ-radiation source. Targeted thymic irradiation (thy-Irr) was performed in a specialized chamber exposing only the mediastinal area to a targeted dose (850 cGy) of X-ray radiation. Dexamethasone (Dex) treatment was performed as previously described (Purton, et al., Expression of the glucocorticoid receptor from the 1A promoter correlates with T lymphocyte sensitivity to glucocorticoid-induced cell death. J Immunol 173:3816 (2004), herein incorporated by reference in their entirety) by giving C57Bl/6 mice 20 mg/kg Dex via intraperitoneal injection and thymuses harvested 5 days after treatment. Cell Isolation. Individual or pooled single cell suspensions of freshly dissected thymuses were obtained by either mechanical dissociation or enzymatic digestion, as previously described (Gray, et al., Unbiased analysis, enrichment and purification of thymic stromal cells. J Immunol Methods 329: 56 (2008), herein incorporated by reference in their entirety). MHCII+ or CD45– cells were enriched by magnetic bead separation using an AutoMACS (Miltenyi Biotech). For experiments involving analysis of thymocyte, LTi or TEC subsets, thymuses were suspended by enzyme-digestion. For ELISA experiments, thymuses were suspended by mechanical dissociation. Reagents. For detection of IL-22 and IL-23, thymus supernatants were obtained by mechanically dissociating thymic tissue in defined volumes of buffer. The resulting supernatant was quantified using cytokine specific ELISA kits purchased from Biolegend (San Diego, USA) and read on a MRX Revelation Plate Reader (Dynex Technologies). Surface antibodies against Ly51 (6C3), CD11c (HL3), CD8 (53-6.7), CD45 (30-F11), CD19 (1D3), CD11b (M1/70), Ly6G (RB6-8C5), TER-119 (TER-119), TCRβ (H57-597), CD3 (145-2C11), CD25 (PC61), CD45R (RA3-6B2), CD45.1 (A20), CD45.2 (104), H-2 Kb (AF6-88.5), CCR6 (140706), ckit (2B8) and CD103 (M290) were purchased from BD Biosciences; antibodies against IL-22 (1H8PWSR), IL-23 (C17.8), RORγ(t) (B2D), EpCAM (G8.8), IL-7Rα (A7R34), NKp46 (29A1.4), RANKL (IK22-5) and CD44 (IM7) were purchased from eBioscience, San Diego, USA; anti-CD90.2 (30-H12) and IA/IE and CD44 (IM7) were purchased from eBioscience; anti-CD90.2 (30-H12) and IA/IE (M5/114.15.2) were purchased from Biolegend, San Diego, USA; anti-CD4 (RM4-5) Qdot 605, CD45R (RA3-6B2) Qdot 655 and streptavidin-conjugates of Qdots 655 and 705 were purchased from Invitrogen; anti-IL-22Rα (496514) and IL-23R were purchased from R&D (Minneapolis, USA). Ulex europaeus agglutinin 1 (UEA-1), conjugated to FITC or Biotin was purchased from Vector Laboratories (Burlingame, Calif.). Flow cytometric analysis was performed on an LSRII (BD Biosciences) and cells were sorted on an Aria II (BD Biosciences) using FACSDiva (BD Biosciences) or FlowJo (Treestar Software). Recombinant mouse IL-22 was purchased from GenScript (New Jersey, USA) or Insight Biotechnology (Wembley, UK), Intracellular staining. For assays requiring analysis of intracellular cytokines or phospho-STATs, cells were fixed and permeabilized in 1.6% paraformaldehyde at 37° C. followed by 90% methanol at 4° C. After thorough washing to remove methanol, cells were stained for both intracellular and extracellular antigens simultaneously. For intracellular IL-22 staining, cells were incubated for 3 hours with Brefeldin A (3 µg/mL). For IL-23 stimulation experiments, cells were first incubated for 1 hour with IL-23 (60 ng/mL; similar results should be observed between 20-2000 ng/ml) then 3 hours with Brefeldin A. For intracellular IL-23 staining Monensin (2 µM) was used in place of Brefeldin A.

Statistics. Statistical analysis between two groups was performed with the nonparametric, unpaired Mann-Whitney U test and between three groups or more with the nonparametric Kruskal-Wallis test (with post-test comparison to untreated or WT control samples). FIGS. 11J, 13C-D and 19C used nonparametric Wilcoxon matched pairs test. Correlations were calculated using the nonparametric Spearman correlation test. Statistics were calculated and display graphs generated using Graphpad Prism.

Example 23

An IL-22 Expression Construct.

The inventors contemplated inserting IL-22 into a vector for use in transfection of precursor T cells in order to enhance thymopoiesis and increase progenitor lymphoid cells in bone marrow, such as increasing production of single positive T cells and increasing B cell production, respectively. Targeting IL-22 expression into areas where contemplated IL-22 production occurs in vivo would have an effect on the appropriate tissues for regeneration or increased function.

Therefore, in one embodiment, a method of IL-22 administration comprises an IL-22 expression construct. An exemplary construct is a lentivirus construct comprising, in between Long Terminal Repeat (LTR) regions in operable order, a human promoter, such as a phosphoglycerate kinase promoter (hPGK), and a human IL-22 (IL22) gene, wherein said gene encodes at least a protein fragment up to a full-length gene capable of encoding a protein for inducing IL-22 function, and a woodchuck hepatitis virus post-transcription regulatory element (WPRE). In one embodiment, the vector construct co-expresses a maker along with an IL-22 active protein. Thus, in another embodiment, an exemplary construct is a lentivirus construct comprising, in between Long Terminal Repeat (LTR) regions in operable order, a human promoter, such as a phosphoglycerate kinase promoter (hPGK), a reporter molecule, i.e. open reading frame (ORF) of enhanced Green Fluorescent Protein (eGFP), a 2A peptide linker sequence (P2A) for linking the eGFP protein with the IL-22 protein, a human IL-22 (L22) gene, wherein said gene encodes at least a protein fragment up to a full-length gene capable of encoding a protein for inducing IL-22 function, and a woodchuck hepatitis virus post-transcription regulatory element (WPRE). As one example, FIG. 26 shows an exemplary strategy to administer IL-22 post-hematopoietic stem cell transplant (HSCT). In FIG. 26 (A) an exemplary Lentiviral construct was made for constitutive IL-22 production and detection by GFP expression. This construct was used to transfect human 293T cells expressing a large T antigen where 26B shows an exemplary quantitative and qualitative comparison of GFP expression in transfected vs. untransfected 293T cells after 72 hour culture by flow cytometry. In FIG. 26(C) nano particles were generated and loaded with Fitc-dextran. Flow cytometry and microscopy showing Fitc+ preT cells.

These studies demonstrated, as a proof-of-principle, that IL-22 was capable of being loaded either transgenically into preT cells, or alternatively loaded into nano-particles then attached to the surface of transplantable preT cells. Thus administration of IL-22 expressing cells or IL-22 protein loaded cells is contemplated to aid in thymic recovery by directly aiding in the proliferation of the supporting microenvironment. Additionally, the use of treatments comprising IL-22 expressing or loaded cells is contemplated to aid patients in the supply of hematopoietic progenitors that can be harnessed for thymopoiesis. Thus in some contemplated embodiments, methods comprising IL-22 constructs and/or IL-22 proteins further comprise using T cells, such as allogeneic T cells, to aid in enhancing thymopoiesis. For some examples of methods using T cells for use in the present inventions, see, Zakrzewski Nat Med 12:1039-1047 (2006); Zakrzewski Nat Biotech 40(1):44-47 (2008); United States Patent Application No. 20110052554, all of which are herein incorporated by reference in their entirety).

Additionally, the inventors contemplated the use of recombinant IL-22 in a vector for use in subjects for boosting immune responses to vaccines.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention should not be unduly limited to such specific embodiments. Indeed, various modifications of the described modes for carrying out the invention which are obvious to those skilled in medicine, diagnostics, evolutionary biology, molecular biology or related fields are intended to be within the scope of the present invention and the following Claims.

We claim:

1. A method of treatment for increasing thymic epithelial cell (TEC) function, comprising:
    a) contacting thymic epithelial cells at least a portion of which have reduced function with IL-22 wherein IL-22 improves the function of said portion of thymic epithelial cells having reduced function.

2. The method of claim 1, wherein said IL-22 is human IL-22.

3. The method of claim 1, wherein said function of said thymic epithelial cells is ability to promote development of mature thymocytes.

4. The method of claim 1, wherein said reduced function of thymic epithelial cells is characterized by a lower number of mature functional thymocytes.

5. The method of claim 1, wherein said increased function of thymic epithelial cells is ability to promote development of mature thymocytes.

6. The method of claim 1, wherein said increased function of said thymic epithelial cells is characterized by an increased number of mature functional thymocytes.

7. The method of claim 1, further comprising administering IL-23.

8. The method of claim 1, wherein said reduced function of thymic epithelial cells is characterized by a lower number of mature functional T-cells.

9. The method of claim 1, wherein contacting said thymic epithelial cells with IL-22 is in vivo.

10. The method of claim 1, wherein contacting said thymic epithelial cells with IL-22 is in vitro.

* * * * *

UNITED STATES PATENT AND TRADEMARK OFFICE
CERTIFICATE OF CORRECTION

Page 1 of 1

| | |
|---|---|
| PATENT NO. | : 9,119,824 B2 |
| APPLICATION NO. | : 13/474319 |
| DATED | : September 1, 2015 |
| INVENTOR(S) | : Marcel R M Van Den Brink |

It is certified that error appears in the above-identified patent and that said Letters Patent is hereby corrected as shown below:

Specification

In column 1, beginning at line 10 and ending at line 17, please delete:

"This invention was made with government support from the National Institutes of Health; grant numbers R01HL69929, CA107096, AI080455 and HL095075 in addition to the United States Department of Defense USAMRAA Award W81XWH-09-1-0294 and the Radiation Effects Research Foundation (RERF-NIAID). The United States Government has certain rights in the invention."

and insert:

--This invention was made with government support under grant numbers: HL069929, AI080455, HL095075, CA107096 and AI101406 awarded by National Institutes of Health, and grant number W81XWH-09-1-0294 awarded by the Army Medical Research and Materiel Command. The government has certain rights in the invention.--

Signed and Sealed this
Seventeenth Day of May, 2016

Michelle K. Lee
*Director of the United States Patent and Trademark Office*